United States Patent
Guillemin et al.

(10) Patent No.: US 9,044,434 B2
(45) Date of Patent: Jun. 2, 2015

(54) METHOD OF INCREASING EPITHELIAL CELL PROLIFERATION WITH CHITIN BINDING PROTEIN

(71) Applicants: Karen Guillemin, Eugene, OR (US); Allison Banse, Eugene, OR (US)

(72) Inventors: Karen Guillemin, Eugene, OR (US); Allison Banse, Eugene, OR (US)

(73) Assignee: State of Oregon, Acting by and Through the State Board of Higher Education on behalf of University of Oregon, Eugene, OR (US)

( * ) Notice: Subject to any disclaimer, the term of this patent is extended or adjusted under 35 U.S.C. 154(b) by 52 days.

(21) Appl. No.: 14/060,392

(22) Filed: Oct. 22, 2013

(65) Prior Publication Data

US 2014/0113873 A1  Apr. 24, 2014

Related U.S. Application Data

(60) Provisional application No. 61/716,991, filed on Oct. 22, 2012.

(51) Int. Cl.
  *A61K 39/106* (2006.01)
  *A61K 38/16* (2006.01)
  *G01N 33/68* (2006.01)
  *G01N 33/574* (2006.01)

(52) U.S. Cl.
  CPC .......... *A61K 38/164* (2013.01); *G01N 33/6893* (2013.01); *G01N 33/57419* (2013.01); *G01N 2333/195* (2013.01); *G01N 2800/065* (2013.01)

(58) Field of Classification Search
  CPC .................................................. A61K 38/164
  USPC ................................ 424/261.1; 514/1.1, 21.2
  See application file for complete search history.

(56) References Cited

PUBLICATIONS

Bowie et al. Deciphering the Message in Protein Sequences: Tolerance to Amino Acid Substitutions. Science, 247:1306-1310, 1990.*
Whisstock et al. Prediction of protein function from protein sequence and structure. Quarterly Reviews in Biophysics. 36(3):307-340, 2007.*
Lazar et al. Transforming Growth Factor alpha: Mutation of Aspartic Acid 47 and Leucine 48 Results in Different Biological Activities. Molecular Cell Biology, 8:1247-1252, 1988.*
Banse et al., "Microbial Regulation of Intestinal Epithelial Cell Proliferation," 4th *ASM Conference on Beneficial Microbes*, Oct. 22-26, 2012 (2 pages).
Cheesman et al., "Epithelial Cell Proliferation in the Developing Zebrafish Intestine is Regulated by the Wnt Pathway and Microbial Signaling via Myd88," *Proc. Natl. Acad. Sci. USA* vol. 108, pp. 4570-4577, 2011.
Vaaje-Kolstad et al., "Crystal Structure and Binding Properties of the *Serratia marcescens* Chitin-Binding Protein CBP21," *J. Biol. Chem.* vol. 280, pp. 11313-11319, 2005.
Wong et al., "The *Vibrio cholerae* Colonization Factor GbpA Possesses a Modular Structure that Governs Binding to Different Host Surfaces," *PLoS Pathogens* vol. 8:e1002373, 2012 (12 pages).

* cited by examiner

*Primary Examiner* — Prema Mertz
(74) *Attorney, Agent, or Firm* — Klarquist Sparkman, LLP

(57) ABSTRACT

Disclosed herein are methods of increasing epithelial cell proliferation (such as intestinal epithelial cell proliferation) by contacting epithelial cells with one or more CBPs. In some examples, the methods include administering the CBP to a subject, such as a subject in need of increased epithelial cell proliferation. Also disclosed herein are methods of identifying a subject having or at risk of developing hyperproliferation of epithelial cells (such as intestinal epithelial cells). Further disclosed are methods of decreasing epithelial cell proliferation by decreasing expression and/or activity of a CBP and methods of identifying inhibitors of epithelial cell proliferation and/or CBP activity.

14 Claims, 9 Drawing Sheets

SEQUENCE LISTING

```
<160> NUMBER OF SEQ ID NOS: 5

<210> SEQ ID NO 1
<211> LENGTH: 473
<212> TYPE: PRT
<213> ORGANISM: Aeromonas veronii

<400> SEQUENCE: 1

Met Ala Ala Lys Ile Gln Leu Asn His Ile Ala Ala Met Leu Ala Leu
1               5                   10                  15

Leu Ala Ser Gly Ser Ala Leu Ala His Gly Tyr Ile Ser Gln Pro Glu
            20                  25                  30

Ser Arg Asn Tyr Leu Cys Lys Thr Gly Gly Asn Ser Gln Cys Gly Gly
        35                  40                  45

Val Gln Trp Glu Pro Gln Ser Val Glu Gly Pro Ser Gly Phe Pro Gln
    50                  55                  60

Thr Gly Pro Gln Asp Gly Gln Ile Ala Ser Ala Gly Ser Pro Arg Trp
65                  70                  75                  80

Ser Glu Leu Asn Ile Gln Thr Ser Asp Arg Trp Thr Lys Arg Glu Val
                85                  90                  95

Gln Pro Gly Pro Phe Ala Ile Ser Trp Thr Phe Thr Ala Asn His Val
            100                 105                 110

Thr Arg Asn Trp Arg Tyr Tyr Leu Thr Lys Gln Glu Trp Asn Pro Asn
        115                 120                 125

Gln Pro Leu Thr Arg Ala Ser Phe Asp Leu Thr Pro Phe Cys Val Ile
    130                 135                 140

Asp Gly Asn Met Val Gln Pro Pro Lys Gln Val Thr His Asn Cys Val
145                 150                 155                 160

Leu Pro Glu Arg Thr Gly Tyr Gln Val Ile Leu Gly Val Trp Glu Val
```

```
            165                 170                 175
Gly Asp Thr Ser Asn Ser Phe Tyr Asn Ile Ile Asp Ala Lys Phe Lys
            180                 185                 190

Asp Gly Ser Gln Pro Pro Leu Glu Trp Ser Gln Ala Gly Thr Ile Tyr
        195                 200                 205

Pro Ser Ile Asp Leu Ala Val Gly Asp Lys Ala Met Thr Arg Val Phe
210                 215                 220

Asp Ala Asn Gly Glu Arg Pro Asp Leu Gln Thr Val Leu Thr Ile Thr
225                 230                 235                 240

Thr Ala Glu Gln Gly Gln Lys Asn Ser Trp Ala His Ala Leu Ala Ser
            245                 250                 255

Lys Ile Asn Ala Glu Gln Ser Leu Ile Arg Ala Gly Gln Gln Gly Ala
        260                 265                 270

Asp Gly Gln Phe Asn Pro Ile Tyr Gly Met Asn Pro Val Tyr Leu His
    275                 280                 285

Arg Asp Ser Lys Leu Asp Arg Val Glu Ile Asp Leu Gln Gln Leu Gln
290                 295                 300

Pro Pro Val Val Asp Ser Ile Ser Val Ser Gly Leu Ala Ser Asp Tyr
305                 310                 315                 320

Val Leu Glu Asn Gly Lys Ile Thr Leu Asp Phe Thr Val Thr Ala Gln
            325                 330                 335

Gly Asp Leu Ala Val Thr Asn Thr Leu Tyr Asp His Gly Gly Val Ala
        340                 345                 350

Lys Gly Glu Ser Ser Ala Asp Ile Lys Asp Ser Ser His Thr Phe Thr
    355                 360                 365

Met Ala Leu Glu Gly Leu Lys Ala Gly His His Gln Leu Val Ile Lys
370                 375                 380

Ala Thr Pro Lys Ala Gly Gly Glu Thr Ile Gln Gln Thr Met Asp Leu
385                 390                 395                 400

Met Phe Lys Asp Gln Ser Ser Gly Glu Tyr Asp Phe Val Phe Pro Asn
            405                 410                 415

Asn Ile Lys Ser Tyr Thr Ala Gly Thr Lys Val Gln Gln Pro Lys Asn
        420                 425                 430

Gly Lys Val Tyr Gln Cys Lys Pro Phe Pro Tyr Ser Gly Tyr Cys Val
    435                 440                 445

Gln Trp Ala Thr Thr Ala Thr Gln Phe Glu Pro Gly Val Gly Ser His
450                 455                 460

Trp Gln Glu Ala Trp Ile Glu Leu Lys
465                 470

<210> SEQ ID NO 2
<211> LENGTH: 485
<212> TYPE: PRT
<213> ORGANISM: Vibrio cholerae

<400> SEQUENCE: 2

Met Lys Lys Gln Pro Lys Met Thr Ala Ile Ala Leu Ile Leu Ser Gly
1               5                   10                  15

Ile Ser Gly Leu Ala Tyr Gly His Gly Tyr Val Ser Ala Val Glu Asn
            20                  25                  30

Gly Val Ala Glu Gly Arg Val Thr Leu Cys Lys Phe Ala Ala Asn Gly
        35                  40                  45

Thr Gly Glu Lys Asn Thr His Cys Gly Ala Ile Gln Tyr Glu Pro Gln
    50                  55                  60
```

-continued

```
Ser Val Glu Gly Pro Asp Gly Phe Pro Val Thr Gly Pro Arg Asp Gly
 65                  70                  75                  80

Lys Ile Ala Ser Ala Glu Ser Ala Leu Ala Ala Leu Asp Glu Gln
                 85                  90                  95

Thr Ala Asp Arg Trp Val Lys Arg Pro Ile Gln Ala Gly Pro Gln Thr
                100                 105                 110

Phe Glu Trp Thr Phe Thr Ala Asn His Val Thr Lys Asp Trp Lys Tyr
                115                 120                 125

Tyr Ile Thr Lys Pro Asn Trp Asn Pro Asn Gln Pro Leu Ser Arg Asp
                130                 135                 140

Ala Phe Asp Leu Asn Pro Phe Cys Val Glu Gly Asn Met Val Gln
145                 150                 155                 160

Pro Pro Lys Arg Val Ser His Glu Cys Ile Val Pro Glu Arg Glu Gly
                165                 170                 175

Tyr Gln Val Ile Leu Ala Val Trp Asp Val Gly Asp Thr Ala Ala Ser
                180                 185                 190

Phe Tyr Asn Val Ile Asp Val Lys Phe Asp Gly Asn Gly Pro Val Leu
                195                 200                 205

Pro Asp Trp Asn Pro Ala Gly Gln Ile Ile Pro Ser Met Asp Leu Ser
210                 215                 220

Ile Gly Asp Thr Val Tyr Thr Arg Val Phe Asp Asn Asp Gly Glu Asn
225                 230                 235                 240

Pro Ala Tyr Arg Thr Glu Leu Lys Ile Asp Ser Glu Thr Leu Thr Lys
                245                 250                 255

Ala Asn Gln Trp Ser Tyr Ala Leu Ala Thr Lys Ile Asn Gln Thr Gln
                260                 265                 270

Lys Gln Gln Arg Ala Gly Gln Leu Asn Gly Asp Gln Phe Val Pro Val
                275                 280                 285

Tyr Gly Thr Asn Pro Ile Tyr Leu Lys Glu Gly Ser Gly Leu Lys Ser
                290                 295                 300

Val Glu Ile Gly Tyr Gln Ile Glu Ala Pro Gln Pro Glu Tyr Ser Leu
305                 310                 315                 320

Thr Val Ser Gly Leu Ala Lys Glu Tyr Glu Ile Gly Glu Gln Pro Ile
                325                 330                 335

Gln Leu Asp Leu Thr Leu Glu Ala Gln Gly Glu Met Ser Ala Glu Leu
                340                 345                 350

Thr Val Tyr Asn His His Gln Lys Pro Leu Ala Ser Trp Ser Gln Ala
                355                 360                 365

Met Thr Asp Gly Glu Leu Lys Ser Ile Thr Leu Glu Leu Ser Glu Ala
                370                 375                 380

Lys Ala Gly His His Met Leu Val Ser Arg Ile Lys Asp Arg Asp Gly
385                 390                 395                 400

Asn Leu Gln Asp Gln Gln Thr Leu Asp Phe Met Leu Val Glu Pro Gln
                405                 410                 415

Thr Pro Pro Thr Pro Gly Asp Tyr Asp Phe Val Phe Pro Asn Gly Leu
                420                 425                 430

Lys Glu Tyr Val Ala Gly Thr Lys Val Leu Ala Ser Asp Gly Ala Ile
                435                 440                 445

Tyr Gln Cys Lys Pro Trp Pro Tyr Ser Gly Tyr Cys Gln Gln Trp Thr
                450                 455                 460

Ser Asn Ala Thr Gln Tyr Gln Pro Gly Thr Gly Ser His Trp Glu Met
465                 470                 475                 480

Ala Trp Asp Lys Arg
```

<210> SEQ ID NO 3
<211> LENGTH: 1418
<212> TYPE: DNA
<213> ORGANISM: Aeromonas veronii

<400> SEQUENCE: 3

```
atggcagcaa aaatccaact caatcacatc gcagcggtgc tggctctgct ggccagcggc      60
agcgccctgg ctcatggcta catcagccag ccagagagtc gcaactatct gtgcaaaacc     120
ggcggcaaca gccagtgtgg cggcgtgcag tgggaacccc agagcgtgga gggcccttcc     180
ggcttcccgc agagtggccc gcaggatggt caaatcgcct cggcgggcag cccgcgctgg     240
agcgagctga acatccagac cagcgaccgc tggaccaagc gtgaagtaca gcccggcccc     300
ttcgccatca gctggacctt caccgccaac cacgtcaccc gtaactggcg ctactacctc     360
accaagcagg actggaaccc caaccagccg ctcacccgcg cctcgttcga cctgaccccc     420
ttctgcgtca tcgacggcaa catggtgcag ccgcccaagc aggtgaccca taactgtgtc     480
ctgccggagc gcaccggtta tcaggtgatc ctcggcgtgt gggaagtggg cgacaccagc     540
aacagcttct acaacatcat cgatgccaag ttcaaagatg gcagccagcc gccgctggtg     600
tggagccagg caggcaccat ctaccccctcc atcgacctcg cagtgggtga caaggcgatg     660
acccgggtat tcgatgccaa cggcgagcgc cccgatctgc agaccgtgct gaccatcacc     720
accgccgagc agggccagaa gaacagctgg gctcatgccc tcgccagcaa gatcaacgcc     780
gagcagagcc tgatccgcgc cggtcagcaa ggagccgatg ccagttcaa tccggtctac     840
ggtatgaacc ccatctatct gcatcgagac agcaaactga agcgggtcga gattgacctg     900
caacagcagc aaccgccggt ggtggacagt atcagcgtca gcggtctggc cagcgactat     960
gtgctggaca cggcaaggc aaccctcgat ttcaccgtca ccgcacaggg cgatctggcc    1020
gtcaccaaca ccctctatga ccacggcggc gtggccaagg tgaaagccg tgcagatatc    1080
aaagacagca gccacacctt caccatggcg ctggaagggc tcaaggcagg tcaccaccag    1140
ctggtgatca aggccacccc gaaagcgggc ggcgaggcca tccagcagac catggatctg    1200
atgttcaagg agcagagcag cagcgaatac gacttcgtct tcccgaacaa catcaagtcc    1260
tacaccgccg gaaccaaggt gcagcagccg aaaaatggca aggtctatca gtgcaagccc    1320
ttccctaca acggctactg cgtgcaatgg gccaccaccg ccacccagtt cgagccgggt    1380
gtcggatccc actggcaaga agcctggatt gagctgaa                             1418
```

<210> SEQ ID NO 4
<211> LENGTH: 1422
<212> TYPE: DNA
<213> ORGANISM: Aeromonas veronii

<400> SEQUENCE: 4

```
atggcagcaa aaatccaact caatcacatc gcggcgatgc tggccctgct ggccagcggc      60
agcgccctgg cccacggcta catcagccag cccgagagcc gcaactacct gtgcaaaacc     120
ggtggcaaca gccagtgtgg cggcgtgcag tgggagcccc agagcgtgga gggcccctca     180
ggcttcccgc aaaccggccc gcaggatggt caaatcgcct cggcgggcag cccgcgctgg     240
agcgagctga acatccagac cagcgaccgc tggaccaagc gtgaagtaca gccaggcccc     300
ttcgccatca gctggacctt cactgccaac cacgtcaccc gcaactggcg ctactacctc     360
accaagcagg agtggaaccc caaccagccg ctcacccgcg cctcgttcga cctgaccccc     420
```

```
ttctgcgtca tcgacggcaa tatggtgcag ccgcccaagc aggtgaccca caactgtgtc      480
ctgccggagc gcaccggtta tcaggtgatc ctcggcgtgt gggaagtggg cgataccagc      540
aacagcttct acaacatcat cgatgccaag ttcaaagatg gcagccagcc gccgctggag      600
tggagccagg caggcaccat ctacccctcc atcgacctcg cagtgggtga caaggcgatg      660
acccgggtat cgatgccaa cggcgagcgc cccgatctgc agaccgtgtt gaccatcacc      720
accgccgagc agggccagaa gaacagctgg gctcatgccc tcgccagcaa gatcaacgcc      780
gagcagagcc tgatccgcgc cggtcagcaa ggagccgatg ccagttcaa tccgatctac       840 ggcatgaacc ccgtctatct gcatcgagac agcaaactgg atcgagtcga gattgacctg       900
caacagctgc agccgccagt ggtggacagc atcagcgtca gcggtctggc cagcgactat       960
gtgctggaaa acggcaagat aactctcgat ttcaccgtca ccgcacaggg cgatctggcc      1020
gtcaccaaca ccctctatga ccacggcggt gtcgccaagg gtgaaagcag tgcagatatc      1080
aaagacagca gccacacctt caccatggcg ctggaaggac tcaaggcagg tcaccaccag      1140
ctggtgatca aggccacccc gaaagcgggc ggcgagacca tccagcagac catggacctg      1200
atgttcaagg atcagagcag cggcgaatat gacttcgtct cccgaacaa catcaagtcc       1260 tacaccgccg gtaccaaggt gcagcagccg aaaaatggca aggtctatca gtgcaagccc      1320
ttcccctaca cgcggctactg cgtgcagtgg gccaccaccg ccacccagtt cgagccgggt      1380
gtcggatccc actggcaaga agcctggatt gagctgaagt ga                          1422

<210> SEQ ID NO 5
<211> LENGTH: 1454
<212> TYPE: DNA
<213> ORGANISM: Vibrio cholerae

<400> SEQUENCE: 5
atgaaaaaac aacctaaaat gaccgctatt gccctgatcc tctctggtat cagtggatta        60
gcgtatggac acggctacgt ttccgcagtg gaaaacggtg tcgccgaagg acgtgtcacc      120
ttgtgtaaat ttgccgctaa cggcactgga gagaaaaaca ctcactgtgg cgcgattcaa      180
tacgaaccac aaagtgtcga aggcccagat ggcttcccgg tcactggccc tcgtgatggc      240
aaaattgcca gtgcggaatc ggcactggcg gcagcgctgg atgagcaaac cgccgaccgt      300
tgggtaaagc gcccaattca agctggccca caaaccttcg agtggacgtt caccgccaac      360
cacgtcacaa aggattggaa atactacatt accaaaccaa actggaaccc aaaccagcca      420
ttgtcgcgtg atgcatttga cctcaatccg ttctgtgtcg ttgaaggaaa tatggtgcag      480
ccaccaaaac gtgtcagcca cgaatgtatc gtgcctgagc gcgaagggta tcaggtcatc      540
ctcgccgtat gggatgttgg cgataccgca gcttccttct acaacgtgat cgacgtgaaa      600
tttgacggta acggcccagt gttacccgat ggaacccag caggtcaaat cattccaagt       660
atggatctca gcattggcga taccgtgtac actcgcgtgt tgataacga tggggaaaac      720 cctgcttatc gcactgagct aaaaattgac tctgagacgc taaccaaagc caatcaatgg      780
tcttacgctc tggcgactaa aattaaccaa acgcaaaaac agcaacgtgc tggtcagctt       840
aatggcgatc aatttgttcc cgtttacggc accaaccccga tttatctgaa agaaggcagt      900
ggcttgaaga gtgttgaaat tggctaccaa attgaagcgc acagcctga gtattcactg       960 acggtttctg gtctagcgaa agagtatgag attggcgaac aaccgattca gcttgacctg      1020
actttagaag cgcaaggtga aatgagcgca gagctgaccg tgtataacca ccaccaaaaa      1080
```

```
ccgctggcaa gttggtcaca agcgatgacg gatggcgagc tgaaatccat cacgctagag    1140
ctgagcgaag ctaaagcggg acatcatatg ttggtttctc gcatcaaaga tcgcgatggc    1200
aatctgcaag atcaacaaac tctcgatttc atgctggttg aaccgcaaac accaccaaca    1260
ccgggtgact acgactttgt gttcccgaat ggcctgaaag agtacgtggc tggcaccaaa    1320
gtgctcgcta gtgatggcgc aatctaccaa tgtaagccat ggccatactc tggctactgc    1380
cagcaatgga caagtaacgc tactcaatac caaccgggta ctggcagtca ttgggaaatg    1440
gcgtgggata aacg                                                      1454
```

METHOD OF INCREASING EPITHELIAL CELL PROLIFERATION WITH CHITIN BINDING PROTEIN

CROSS REFERENCE TO RELATED APPLICATION

Benefit is claimed to the earlier filing date of U.S. Provisional Application No. 61/716,991, filed Oct. 22, 2012, which is incorporated herein by reference in its entirety.

FIELD

This disclosure relates to chitin binding proteins and methods of their use, particularly to increase or decrease epithelial cell proliferation.

BACKGROUND

The resident microbial community of the intestine (intestinal microbiota) affects homeostasis of the intestinal epithelium in vertebrates and is a potential contributor to hyperproliferative diseases of the intestinal epithelium. There is a need to understand how microbial signals contribute to intestinal epithelium homeostasis and how these signals may also contribute to hyperproliferative diseases.

SUMMARY

Disclosed herein are chitin binding proteins (CBPs) isolated from intestinal microbiota, such as *Aeromonas veronii* and *Vibrio cholerae*, which increase epithelial cell proliferation. Also disclosed herein are methods of increasing epithelial cell proliferation (such as intestinal epithelial cell proliferation) by contacting epithelial cells with one or more CBPs, or a portion thereof. In some examples, the methods include administering the CBP (or a portion thereof) to a subject, such as a subject in need of increased epithelial cell proliferation.

Also disclosed herein are methods of identifying a subject having or at risk of developing hyperproliferation of epithelial cells (such as intestinal epithelial cells). The methods include determining presence or amount (for example, expression) of a CBP in a sample from a subject and comparing the expression of CBP in the sample from the subject with a control. An increase in the amount or expression of CBP in the sample from the subject as compared to the control indicates that the subject has or is at risk of developing epithelial cell hyperproliferation. In some examples, the subject has or is suspected of having intestinal epithelial cell hyperproliferation (such as colorectal cancer, inflammatory bowel disease, celiac disease, or diabetes).

Further disclosed herein are methods of decreasing intestinal epithelial cell proliferation (such as intestinal epithelial cell hyperproliferation) in a subject, including administering to the subject a therapeutically effective amount of an agent that alters (for example, decreases) expression or activity of a CBP. In some examples, the disclosed methods include treating intestinal epithelial cell hyperproliferation in a subject by administering a compound that blocks CBP activity. Also disclosed are methods of identifying an inhibitor of epithelial cell proliferation. The methods include contacting epithelial cells (such as intestinal epithelial cells) with a CBP and one or more test compounds and measuring proliferation of the epithelial cells. A compound or combination of compounds that increases epithelial cell proliferation as compared to a control (such as epithelial cells contacted with CBP alone) is identified as a compound that inhibits epithelial cell proliferation.

The foregoing and other features of the disclosure will become more apparent from the following detailed description, which proceeds with reference to the accompanying figures.

SEQUENCE LISTING

Figure 1:
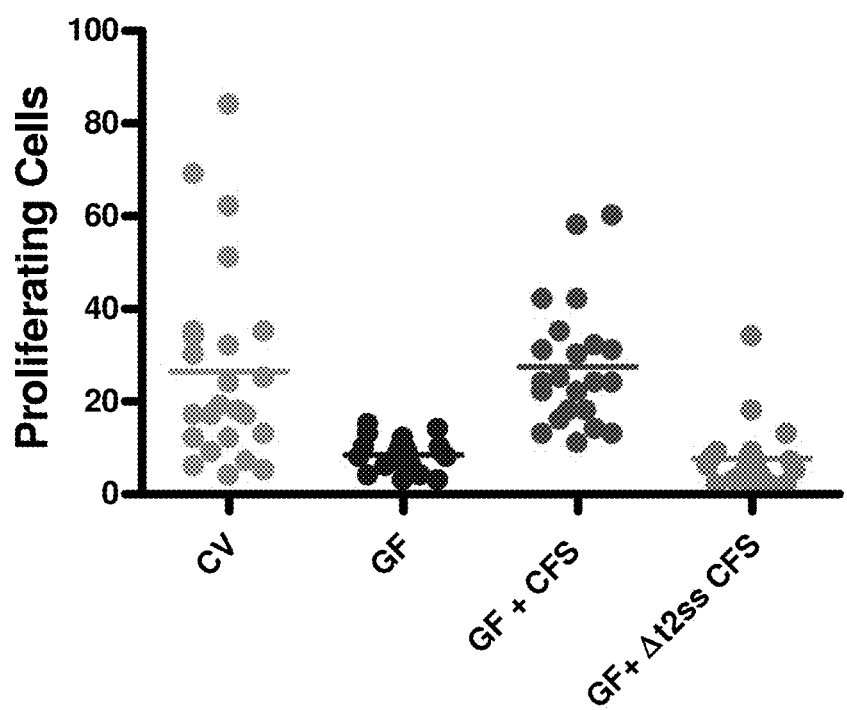
FIG. 1 is a graph showing the number of proliferating intestinal epithelial cells in zebrafish raised conventionally (CV), germ-free (GF), GF with cell-free supernatant (CFS) from *Aeromonas veronii*, or GF with CFS from type II secretion system (T2SS) deletion mutant *A. veronii* (GF+Δt2ss CFS). *, significantly more than GF.

The nucleic and amino acid sequences listed herein are shown using standard letter abbreviations for nucleotide bases, and one letter code for amino acids. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 21, 2013, and is 14,479 bytes, which is incorporated by reference herein.

SEQ ID NO: 1 is an exemplary amino acid sequence of an *A. veronii* CBP.

SEQ ID NO: 2 is an exemplary amino acid sequence of a *V. cholerae* GbpA protein.

SEQ ID NOs: 3 and 4 are exemplary nucleic acid sequences encoding an *A. veronii* CBP.

SEQ ID NO: 5 is an exemplary nucleic acid sequence encoding a *V. cholerae* GbpA protein.

DETAILED DESCRIPTION

I. Abbreviations
CBP chitin binding protein
CFS cell-free supernatant
CV conventionally reared
GbpA N-acetylglucosamine binding protein A
GF germ-free reared
GlcNAc N-acetylglucosamine
T2SS type 2 secretion system II. Terms Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Chitin binding protein (CBP): A protein that binds to chitin, for example through direct binding to chitin or indirect binding to chitin, such as through binding to N-acetylglucosamine (GlcNAc) residues on chitin. In some examples, a CBP may also bind to mucin (directly or indirectly).

An exemplary chitin binding protein includes *A. veronii* chitin binding protein, also referred to as acetylglucosamine-binding protein (exemplified by SEQ ID NO: 1). Another exemplary chitin binding protein includes *V. cholerae* GlcNAc binding protein A (GbpA) (exemplified by SEQ ID NO: 2). One of skill in the art can identify additional CBPs. Additional exemplary CBPs are provided in Section III, below Control: A "control" refers to a sample or standard used for comparison with an experimental sample. In some embodiments, the control is a sample obtained from a healthy subject or healthy tissue. In some embodiments, the control is a historical control or standard reference value or range of values (such as a previously tested control sample, such as a group of samples that represent baseline or normal values).

Hyperproliferation: Excessive growth and/or reproduction of cells (for example, a disruption of normal tissue homeostasis), such as epithelial cells (for example, intestinal epithelial cells). For example, hyperproliferation includes intestinal epithelial cell proliferation that is significantly increased compared to a control, such as normal or healthy intestinal epithelial cells. In some examples, intestinal epithelial cell hyperproliferation includes an increase in epithelial cell proliferation (for example, cell number or rate of division) of at least about 5-fold (such as at least about 10-fold, 20-fold, or more) as compared to a control.

In some examples, hyperproliferation of cells is associated with a disease state, such as cancer (for example, colorectal cancer) or inflammatory bowel disease (such as Crohn's disease, ulcerative colitis, or celiac disease).

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and/or cells. Nucleic acid molecules and proteins that have been "isolated" include nucleic acid molecules and proteins purified by standard purification methods or prepared by recombinant expression in a host cell, as well as chemically synthesized nucleic acid molecules and proteins.

Sample (or biological sample): A specimen containing genomic DNA, RNA (including mRNA), protein, or combinations thereof, obtained from a subject. Examples include, but are not limited to, peripheral blood (or fractions thereof), fine needle aspirate, urine, saliva, feces, tissue biopsy, surgical specimen, and autopsy material. In one example, a sample includes a tumor biopsy (such as a colorectal tumor tissue biopsy) or an intestinal tissue biopsy. In another example, a sample includes isolated tumor cells, such as tumor cells isolated from blood of a subject with a tumor.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

One of skill in the art will appreciate that the particular sequence identity ranges provided herein are for guidance only; it is possible that strongly significant homologs or orthologs could be obtained that fall outside the ranges provided.

Subject: Living multi-cellular vertebrate organism, a category that includes vertebrates, including human and non-human mammals.

Therapeutically effective amount: An amount of an agent or composition that alone, or together with a pharmaceutically acceptable carrier and/or one or more additional therapeutic agents, induces the desired response. Effective amounts of an agent can be determined in many different ways, such as assaying for a reduction in epithelial cell proliferation, delay (or even prevention) of onset of a condition associated with intestinal epithelial cell hyperproliferation (such as colorectal cancer or inflammatory bowel disease), or a reduction or amelioration of one or more symptoms of a subject with intestinal epithelial cell hyperproliferation. Effective amounts also can be determined through various in vitro, in vivo or in situ assays.

III. Chitin Binding Proteins

Disclosed herein are chitin binding proteins, for example, CBPs from members of the intestinal microbiota. In some embodiments, the CBP is an *A. veronii* CBP, such as a polypeptide comprising or consisting of the amino acid sequence set forth as:

SEQ ID NOs: 1 or 2. For example, the polypeptide can have an amino acid sequence with at least 80%, 85%, 90%, 95%, 96%, 97%, 98%, or 99% sequence identity to the amino acid sequences set forth in SEQ ID NOs: 1 or 2. Exemplary sequences can be obtained using computer programs that are readily available on the internet and the amino acid sequences set forth herein. In some examples, the polypeptide retains a function of the CBP, such as stimulating epithelial cell proliferation. In one example, the polypeptide retains binding to chitin, mucin, and/or GlcNAc; however, in some examples, chitin binding, mucin binding, and/or GlcNAc binding is not required.

In additional embodiments, a CBP includes a portion or fragment of a chitin binding protein (for example, a portion of an *A. veronii* CBP or *V. cholerae* GbpA polypeptide disclosed herein). In some examples, the CBP or portion thereof includes at least 20 contiguous amino acids of a CBP, for example, at least 30, at least 50, at least 75, at least 100, at least 150, at least 200, at least 250, at least 300, at least 350, at least 400, at least 450, or more amino acids of a CBP. In particular examples, a portion or fragment of a CBP includes one or more domains of a CBP. In some examples, a first domain (also referred to as domain D1) may include amino acids 24-203 of *V. cholerae* GbpA, a second domain (also referred to as domain D2) may include amino acids 211-310 of *V. cholerae* GbpA, a third domain (also referred to as domain D3) may include amino acids 319-413 of *V. cholerae* GbpA, and a fourth domain (also referred to as domain D4) may include amino acids 423-485 of *V. cholerae* GbpA. In other, non-limiting, examples, an isolated *A. veronii* CBP domain 1

```
MAAKIQLNHIAAMLALLASGSALAHGYISQPESRNYLCKTGGNSQCGGVQWEPQSVEGPSGFPQ    (SEQ ID NO: 1)

TGPQDGQIASAGSPRWSELNIQTSDRWTKREVQPGPFAISWTFTANHVTRNWRYYLTKQEWNPN

QPLTRASFDLTPFCVIDGNMVQPPKQVTHNCVLPERTGYQVILGVWEVGDTSNSFYNIIDAKFK

DGSQPPLEWSQAGTIYPSIDLAVGDKAMTRVFDANGERPDLQTVLTITTAEQGQKNSWAHALAS

KINAEQSLIRAGQQGADGQFNPIYGMNPVYLHRDSKLDRVEIDLQQLQPPVVDSISVSGLASDY

VLENGKITLDFTVTAQGDLAVTNTLYDHGGVAKGESSADIKDSSHTFTMALEGLKAGHHQLVIK

ATPKAGGETIQQTMDLMFKDQSSGEYDFVFPNNIKSYTAGTKVQQPKNGKVYQCKPFPYSGYCV

QWATTATQFEPGVGSHWQEAWIELK
```

In other embodiments, the CBP is a *V. cholerae* CBP, such as a polypeptide comprising or consisting of the amino acid sequence set forth as:

(D1) polypeptide includes amino acids 25-193 of SEQ ID NO: 1 and an isolated *A. veronii* CBP domain 1-3 (D1-D3) polypeptide includes amino acids 25-404 of SEQ ID NO: 1.

```
MKKQPKMTAIALILSGISGLAYGHGYVSAVENGVAEGRVTLCKFAANGTGEKNTHCGAIQYEPQ    (SEQ ID NO: 2)

SVEGPDGFPVTGPRDGKIASAESALAAALDEQTADRWVKRPIQAGPQTFEWTFTANHVTKDWKY

YITKPNWNPNQPLSRDAFDLNPFCVVEGNMVQPPKRVSHECIVPEREGYQVILAVWDVGDTAAS

FYNVIDVKFDGNGPVLPDWNPAGQIIPSMDLSIGDTVYTRVFDNDGENPAYRTELKIDSETLTK

ANQWSYALATKINQTQKQQRAGQLNGDQFVPVYGTNPIYLKEGSGLKSVEIGYQIEAPQPEYSL

TVSGLAKEYEIGEQPIQLDLTLEAQGEMSAELTVYNHHQKPLASWSQAMTDGELKSITLELSEA

KAGHHMLVSRIKDRDGNLQDQQTLDFMLVEPQTPPTPGDYDFVFPNGLKEYVAGTKVLASDGAI

YQCKPWPYSGYCQQWTSNATQYQPGTGSHWEMAWDKR
```

In additional embodiments, a CBP polypeptide disclosed herein has at least 75%, 85%, 90%, 95%, 96%, 97%, 98%, or 99% sequence identity to the amino acid sequence set forth in In some examples, the N-terminal signal sequence of the CBP is not included in domain 1. One of ordinary skill in the art will recognize that the boundaries of the domains D1-D4 are not exact and in some examples may include additional or fewer amino acids (for example, about 20, 19, 18, 17, 16, 15, 14, 13, 12, 11, 10, 9, 8, 7, 6, 5, 4, 3, 2, or 1 more or less amino acids from either end of the domain). Furthermore, one of ordinary skill in the art can identify the corresponding domains from other CBPs, for example a CBP from another bacterium or other organism.

Minor modifications of CBP primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of CBP is a conservative variant of the CBP (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions).

Additional exemplary CBPs include the amino acid sequences of GenBank Accession Nos. ZP_11082707, YP_004394209, EKB21080, YP_001140518, YP_004939473, NP_233197, YP_001215264, and YP_004190719; all of which are incorporated herein by reference as present in GenBank on Oct. 22, 2012. One of ordinary skill in the art can identify additional CBPs, for example from other microbiota.

In additional embodiments, the CBP is encoded by a nucleic acid sequence including or consisting of the nucleic acid sequences set forth as:

```
ATGGCAGCAAAAATCCAACTCAATCACATCGCAGCGGTGCTGGCTCTGCTGGCCAGCGGCAGCG    (SEQ ID NO: 3)

CCCTGGCTCATGGCTACATCAGCCAGCCAGAGAGTCGCAACTATCTGTGCAAAACCGGCGGCAA

CAGCCAGTGTGGCGGCGTGCAGTGGGAACCCCAGAGCGTGGAGGGCCCTTCCGGCTTCCCGCAG

AGTGGCCCGCAGGATGGTCAAATCGCCTCGGCGGGCAGCCCGCGCTGGAGCGAGCTGAACATCC

AGACCAGCGACCGCTGGACCAAGCGTGAAGTACAGCCCGGCCCCTTCGCCATCAGCTGGACCTT

CACCGCCAACCACGTCACCCGTAACTGGCGCTACTACCTCACCAAGCAGGACTGGAACCCCAAC

CAGCCGCTCACCCGCGCCTCGTTCGACCTGACCCCCTTCTGCGTCATCGACGGCAACATGGTGC

AGCCGCCCAAGCAGGTGACCCATAACTGTGTCCTGCCGGAGCGCACCGGTTATCAGGTGATCCT

CGGCGTGTGGGAAGTGGGCGACACCAGCAACAGCTTCTACAACATCATCGATGCCAAGTTCAAA

GATGGCAGCCAGCCGCCGCTGGTGTGGAGCCAGGCAGGCACCATCTACCCCTCCATCGACCTCG

CAGTGGGTGACAAGGCGATGACCCGGGTATTCGATGCCAACGGCGAGCGCCCCGATCTGCAGAC

CGTGCTGACCATCACCACCGCCGAGCAGGGCCAGAAGAACAGCTGGGCTCATGCCCTCGCCAGC

AAGATCAACGCCGAGCAGAGCCTGATCCGCGCCGGTCAGCAAGGAGCCGATGGCCAGTTCAATC

CGGTCTACGGTATGAACCCCATCTATCTGCATCGAGACAGCAAACTGAAGCGGGTCGAGATTGA

CCTGCAACAGCAGCAACCGCCGGTGGTGGACAGTATCAGCGTCAGCGGTCTGGCCAGCGACTAT

GTGCTGGACAACGGCAAGGCAACCCTCGATTTCACCGTCACCGCACAGGGCGATCTGGCCGTCA

CCAACACCCTCTATGACCACGGCGGCGTGGCCAAGGGTGAAAGCCGTGCAGATATCAAAGACAG

CAGCCACACCTTCACCATGGCGCTGGAAGGGCTCAAGGCAGGTCACCACCAGCTGGTGATCAAG

GCCACCCCGAAAGCGGGCGGCGAGGCCATCCAGCAGACCATGGATCTGATGTTCAAGGAGCAGA

GCAGCAGCGAATACGACTTCGTCTTCCCGAACAACATCAAGTCCTACACCGCCGGAACCAAGGT

GCAGCAGCCGAAAAATGGCAAGGTCTATCAGTGCAAGCCCTTCCCCTACAACGGCTACTGCGTG

CAATGGGCCACCACCGCCACCCAGTTCGAGCCGGGTGTCGGATCCCACTGGCAAGAAGCCTGGA

TTGAGCTGAA

ATGGCAGCAAAAATCCAACTCAATCACATCGCGGCGATGCTGGCCCTGCTGGCCAGCGGCAGCG    (SEQ ID NO: 4)

CCCTGGCCCACGGCTACATCAGCCAGCCCGAGAGCCGCAACTACCTGTGCAAAACCGGTGGCAA

CAGCCAGTGTGGCGGCGTGCAGTGGGAGCCCCAGAGCGTGGAGGGCCCCTCAGGCTTCCCGCAA

ACCGGCCCGCAGGATGGTCAAATCGCCTCGGCGGGCAGCCCGCGCTGGAGCGAGCTGAACATCC

AGACCAGCGACCGCTGGACCAAGCGTGAAGTACAGCCAGGCCCCTTCGCCATCAGCTGGACCTT

CACTGCCAACCACGTCACCCGCAACTGGCGCTACTACCTCACCAAGCAGGAGTGGAACCCCAAC

CAGCCGCTCACCCGCGCCTCGTTCGACCTGACCCCCTTCTGCGTCATCGACGGCAATATGGTGC
```

-continued

```
AGCCGCCCAAGCAGGTGACCCACAACTGTGTCCTGCCGGAGCGCACCGGTTATCAGGTGATCCT

CGGCGTGTGGGAAGTGGGCGATACCAGCAACAGCTTCTACAACATCATCGATGCCAAGTTCAAA

GATGGCAGCCAGCCGCCGCTGGAGTGGAGCCAGGCAGGCACCATCTACCCCTCCATCGACCTCG

CAGTGGGTGACAAGGCGATGACCCGGGTATTCGATGCCAACGGCGAGCGCCCCGATCTGCAGAC

CGTGTTGACCATCACCACCGCCGAGCAGGGCCAGAAGAACAGCTGGGCTCATGCCCTCGCCAGC

AAGATCAACGCCGAGCAGAGCCTGATCCGCGCCGGTCAGCAAGGAGCCGATGGCCAGTTCAATC

CGATCTACGGCATGAACCCCGTCTATCTGCATCGAGACAGCAAACTGGATCGAGTCGAGATTGA

CCTGCAACAGCTGCAGCCGCCAGTGGTGGACAGCATCAGCGTCAGCGGTCTGGCCAGCGACTAT

GTGCTGGAAAACGGCAAGATAACTCTCGATTTCACCGTCACCGCACAGGGCGATCTGGCCGTCA

CCAACACCCTCTATGACCACGGCGGTGTCGCCAAGGGTGAAAGCAGTGCAGATATCAAAGACAG

CAGCCACACCTTCACCATGGCGCTGGAAGGACTCAAGGCAGGTCACCACCAGCTGGTGATCAAG

GCCACCCCGAAAGCGGGCGGCGAGACCATCCAGCAGACCATGGACCTGATGTTCAAGGATCAGA

GCAGCGGCGAATATGACTTCGTCTTCCCGAACAACATCAAGTCCTACACCGCCGGTACCAAGGT

GCAGCAGCCGAAAAATGGCAAGGTCTATCAGTGCAAGCCCTTCCCCTACAGCGGCTACTGCGTG

CAGTGGGCCACCACCGCCACCCAGTTCGAGCCGGGTGTCGGATCCCACTGGCAAGAAGCCTGGA

TTGAGCTGAAGTGA

ATGAAAAAACAACCTAAATGACCGCTATTGCCCTGATCCTCTCTGGTATCAGTGGATTAGCGT    (SEQ ID NO: 5)

ATGGACACGGCTACGTTTCCGCAGTGGAAAACGGTGTCGCCGAAGGACGTGTCACCTTGTGTAA

ATTTGCCGCTAACGGCACTGGAGAGAAAAACACTCACTGTGGCGCGATTCAATACGAACCACAA

AGTGTCGAAGGCCCAGATGGCTTCCCGGTCACTGGCCCTCGTGATGGCAAAATTGCCAGTGCGG

AATCGGCACTGGCGGCAGCGCTGGATGAGCAAACCGCCGACCGTTGGGTAAAGCGCCCAATTCA

AGCTGGCCCACAAACCTTCGAGTGGACGTTCACCGCCAACCACGTCACAAAGGATTGGAAATAC

TACATTACCAAACCAAACTGGAACCCAAACCAGCCATTGTCGCGTGATGCATTTGACCTCAATC

CGTTCTGTGTCGTTGAAGGAAATATGGTGCAGCCACCAAAACGTGTCAGCCACGAATGTATCGT

GCCTGAGCGCGAAGGGTATCAGGTCATCCTCGCCGTATGGGATGTTGGCGATACCGCAGCTTCC

TTCTACAACGTGATCGACGTGAAATTTGACGGTAACGGCCCAGTGTTACCCGATTGGAACCCAG

CAGGTCAAATCATTCCAAGTATGGATCTCAGCATTGGCGATACCGTGTACACTCGCGTGTTTGA

TAACGATGGGGAAAACCCTGCTTATCGCACTGAGCTAAAAATTGACTCTGAGACGCTAACCAAA

GCCAATCAATGGTCTTACGCTCTGGCGACTAAAATTAACCAAACGCAAAAACAGCAACGTGCTG

GTCAGCTTAATGGCGATCAATTTGTTCCCGTTTACGGCACCAACCCGATTTATCTGAAAGAAGG

CAGTGGCTTGAAGAGTGTTGAAATTGGCTACCAAATTGAAGCGCCACAGCCTGAGTATTCACTG

ACGGTTTCTGGTCTAGCGAAAGAGTATGAGATTGGCGAACAACCGATTCAGCTTGACCTGACTT

TAGAAGCGCAAGGTGAAATGAGCGCAGAGCTGACCGTGTATAACCACCACCAAAAACCGCTGGC

AAGTTGGTCACAAGCGATGACGGATGGCGAGCTGAAATCCATCACGCTAGAGCTGAGCGAAGCT

AAAGCGGGACATCATATGTTGGTTTCTCGCATCAAAGATCGCGATGGCAATCTGCAAGATCAAC

AAACTCTCGATTTCATGCTGGTTGAACCGCAAACACCACCAACACCGGGTGACTACGACTTTGT

GTTCCCGAATGGCCTGAAAGAGTACGTGGCTGGCACCAAAGTGCTCGCTAGTGATGGCGCAATC

TACCAATGTAAGCCATGGCCATACTCTGGCTACTGCCAGCAATGGACAAGTAACGCTACTCAAT

ACCAACCGGGTACTGGCAGTCATTGGGAAATGGCGTGGGATAAACG
```

In additional embodiments, a nucleic acid encoding a CBP polypeptide disclosed herein has at least 75%, 85%, 90%, 95%, 96%, 97%, 98%, or 99% sequence identity to the nucleic acid sequence set forth in SEQ ID NOs: 3-5. For example, the nucleic acid can have a nucleic acid sequence with at least 80%, 85%, 90%, 95%, 96%, 97%, 98%, or 99% sequence identity to the nucleic acid sequences set forth in SEQ ID NOs: 3-5. Exemplary sequences can be obtained using computer programs that are readily available on the internet and the amino acid sequences set forth herein. In some examples, the nucleic acid encodes a polypeptide that retains a function of the CBP, such as stimulating epithelial cell proliferation. In one example, the nucleic acid encodes a polypeptide that retains binding to chitin, mucin, and/or GlcNAc; however, in some examples, chitin binding, mucin binding, and/or GlcNAc binding is not required.

Additional exemplary CBPs include the amino acid sequences of GenBank Accession Nos. CP002607 (nucleotides 3994027-3995444), CP000644 (nucleotides 610550-609130 (reverse complement)), CP000462 (nucleotides 649265-647854 (reverse complement)), AJFN02000046 (nucleotides 21733-20280 (reverse complement)), CP003331 (nucleotides 755303-756756), CP003070 (nucleotides 456010-457463), CP001486 (nucleotides 590354-588901 (reverse complement)), EU072441, and DQ082856; all of which are incorporated herein by reference as present in GenBank on Oct. 12, 2013. One of ordinary skill in the art can identify additional nucleic acid sequences encoding CBPs, for example, from other microbiota.

IV. Methods of Increasing Cell Proliferation

Disclosed herein are methods of increasing cell proliferation (such as epithelial cell proliferation). In some embodiments, the methods include contacting an epithelial cell (such as an intestinal epithelial cell) with a chitin binding protein, including, but not limited to the CBPs disclosed herein. In some examples, the CBP is an isolated CBP, such as a purified or partly purified CBP. In some examples, the CBP is in the form of a supernatant from a bacterial culture (such as an *Aeromonas veronii* or *Vibrio cholerae* culture), which may be concentrated or filtered (for example, to remove components below a selected molecular weight cutoff, such as 10 kD). In other examples, the CBP is a recombinant CBP, for example expressed in and/or purified from another cell, such as *E. coli*. In other examples, the CBP is present in or produced by an organism (such as *Aeromonas* spp. or *Vibrio* spp.). For example, in some embodiments, the methods include contacting an epithelial cell with a bacterium that expresses a CBP or portion thereof (such as *A. veronii* or *V. cholerae*).

The disclosed methods include contacting one or more epithelial cells with a CBP in order to increase epithelial cell proliferation. In some examples, the cells are contacted with the CBP in vitro. In other examples, the methods include contacting epithelial cells with CBP by administering an effective amount of a CBP to a subject. The CBP may be administered in any form, including administration of cells producing a CBP (e.g., *A. veronii, V. cholerae*, or bacteria recombinantly expressing or overexpressing a CBP), a cell extract or preparation (such as a cell-free supernatant) from a cell producing a CBP, an isolated or purified CBP polypeptide (including, but not limited to SEQ ID NOs: 1 or 2), or a nucleic acid encoding a CBP (including, but not limited to, SEQ ID NOs: 3-5).

The CBP polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding CBP or a portion thereof into an expression vector, introducing the expression vector into a host cell (such as *E. coli*), and isolating the polypeptide.

In some embodiments, the CBP is administered to a subject in need of increased intestinal cell proliferation. In some examples, the subject may have one of a number of conditions broadly categorized as short bowel syndrome (including congenital short bowel, surgical removal of a portion of the intestine, or dysfunction of a large segment of bowel). In other examples, the subject may have had a portion of the gastrointestinal tract removed, for example to treat Hirschsprung's disease or necrotizing enterocolitis.

The CBP can be administered to a subject in need of treatment using any suitable means known in the art. Methods of administration include, but are not limited to, intradermal, intramuscular, intraperitoneal, parenteral, subcutaneous, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent. In particular examples, the CBP is administered orally.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic agents Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

The amount of CBP to be used to contact the epithelial cells or administered to a subject can be selected by one of ordinary skill in the art, for example from about 1 μg to 1 g CBP (such as about 10 μg to 500 mg, 100 μg to 100 mg, or 1 mg to 10 mg). In some examples, an effective amount of CBP is an amount that increases epithelial cell proliferation, such as intestinal epithelial cell proliferation.

V. Methods of Identifying Intestinal Epithelial Cell Hyperproliferation

Disclosed herein are methods of identifying a subject as having or being at risk of epithelial cell hyperproliferation (such as intestinal epithelial cell hyperproliferation). In some examples, the subject is one that is known to have one or more risk factors for epithelial cell hyperproliferation, such as a subject with one or more risk factors for cancer (such as colorectal cancer or gastric cancer), inflammatory bowel disease, celiac disease, and/or diabetes. Thus, in some examples, the subject has a family history of colorectal cancer or has one or more genetic risk factors for colorectal cancer (for example, one or more mutations in APC, TP53, STK11, PTEN, BMPR1A, SMAD4, MLH1, MSH2, MSH6, PMS2, EPCAM, MYH, and/or AXIN1). In other examples, the subject is not known to have any risk factors for intestinal epithelial cell hyperproliferation.

In some embodiments, the methods include determining the presence or amount of a CBP in a sample from the subject and comparing the presence or amount of CBP with a control. An increased amount of the CBP in the sample from the subject (such as a statistically significant increase) as compared to the control identifies the subject as having or being at risk of intestinal epithelial cell hyperproliferation. In some examples, the CBP includes those described in Section III, including, but not limited to SEQ ID NOs: 1 or 2 or proteins with at least 75% sequence identity to SEQ ID NOs: 1 or 2.

In some embodiments, the increase in expression of CBP in a sample from the subject is at least 1.5-fold, at least 2-fold, at least 2.5-fold, at least 3-fold, at least 4-fold, at least 5-fold, at least 7-fold or at least 10-fold relative to a control sample. An increase in expression (such as amount or presence of CBP) in a sample from a subject as compared to a control indicates that the subject has or is at risk of developing intestinal epithelial cell hyperproliferation. In some examples, the subject has or is at risk of developing intestinal epithelial cell hyperproliferation, such as cancer (for example, colorectal cancer), chronic inflammation such as inflammatory bowel disease, irritable bowel syndrome, celiac disease, or diabetes. In a particular example, the subject may have a genetic predisposition to develop colorectal cancer, such as a mutation associated with hereditary nonpolyposis colon cancer, familial adenomatous polyposis, MYH-associated polyposis, Peutz-Jeghers syndrome, juvenile polyposis syndrome, or PTEN hamartoma tumor syndrome.

The sample from the subject can be any sample that includes CBP protein or nucleic acid. In some examples, the sample includes blood, fine needle aspirate, urine, saliva, feces, tissue biopsy, surgical specimen, and autopsy material. In one example, a sample includes a tumor biopsy (such as a colorectal tumor tissue biopsy) or an intestinal tissue biopsy.

The control can be any suitable control against which to compare expression of CBP in a sample. In some embodiments, the sample from the subject is tumor tissue (such as colorectal tumor tissue) and the control sample is non-tumor tissue. In some examples, the non-tumor tissue is obtained from the same subject, such as non-tumor tissue that is adjacent to the tumor. In other examples, the non-tumor tissue is obtained from a healthy control subject. In other embodiments, the sample from the subject is intestinal tissue and the control sample is intestinal tissue from a healthy control subject. In other embodiments, the control is a reference value or ranges of values. For example, the reference value can be derived from the average expression values obtained from a group of healthy control subjects or non-tumor tissue from a group of cancer patients.

Presence or amount (for example, expression) of a CBP can be detected using any one of a number of methods well known in the art. Although exemplary methods are provided, the disclosure is not limited to such methods. Expression of either mRNA or protein is contemplated herein.

Gene expression can be evaluated by detecting mRNA encoding the gene of interest. Thus, the disclosed methods can include detecting and/or quantitating mRNA encoding CBP. In some examples, the mRNA is quantitated. RNA can be isolated from a sample from a subject using methods well known to one of ordinary skill in the art, including commercially available kits.

Methods of detecting gene expression include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); or PCR-based methods, such as reverse transcription polymerase chain reaction (RT-PCR) (Weis et al., *Trends in Genetics* 8:263-4, 1992) or real-time PCR. Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR or real-time RT-PCR can be used to compare mRNA levels in different samples, in subject and control samples to characterize patterns of gene expression, to discriminate between closely related mRNAs, and to analyze RNA structure.

In some examples, expression of CBP protein is analyzed. Any standard immunoassay format (such as ELISA, Western blot, or radioimmunoas say) can be used to measure protein levels. Thus, in one example, polypeptide levels of CBP in a sample can readily be evaluated using these methods. Immunohistochemical techniques can also be utilized for CBP polypeptide detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

Antibodies specific for a CBP (such as SEQ ID NO: 1 or 2) can be used for detection and quantitation of CBP by one of a number of immunoassay methods that are well known in the art, such as those presented in Harlow and Lane (*Antibodies, A Laboratory Manual*, CSHL, New York, 1988). Methods of constructing such antibodies are known in the art. In addition, such antibodies may be commercially available.

In some embodiments, the disclosed methods further comprise administering an inhibitor of a chitin binding protein to a subject who is identified as having or being at risk of intestinal epithelial cell hyperproliferation. Inhibitors of a chitin binding protein (such as an inhibitor of a CBP disclosed herein) and their administration to a subject are discussed in Section VI, below.

VI. Methods of Decreasing Epithelial Cell Proliferation

Disclosed herein are methods of decreasing intestinal epithelial cell proliferation (such as intestinal epithelial cell hyperproliferation) in a subject, including administering to the subject a therapeutically effective amount of an agent that alters (for example, decreases) expression or activity of a CBP. Such agents can alter the expression of nucleic acid sequences (such as DNA, cDNA, or mRNAs) or proteins. In other examples, the agent decreases at least one biological activity of a CBP, such as binding to chitin, mucin, and/or GlcNAc, and/or stimulation of epithelial cell proliferation. In additional embodiments, the disclosed methods include treating intestinal epithelial cell hyperproliferation in a subject by administering a compound that blocks CBP activity. An alteration in the expression or activity can be any detectable increase or decrease that results in a biological effect. For example, an agent can increase or decrease the expression or activity by a desired amount, for example by at least about 1.5-fold, at least about 2-fold, at least about 2.5-fold, at least about 3-fold, at least about 4-fold, at least about 5-fold, at least about 7-fold, or at least about 10-fold relative to activity or expression in a control (for example the relative amount of expression or activity in the absence of treatment).

Decreasing intestinal epithelial cell hyperproliferation and/or treating intestinal epithelial cell hyperproliferation in a subject can include reducing and/or delaying the development of intestinal epithelial cell hyperproliferation in the subject. Such reduced intestinal epithelial cell hyperproliferation can in some examples decrease intestinal epithelial cell proliferation by at least 10%, at least 20%, at least 50%, or at least 75%. In other embodiments, decreasing or treating intestinal epithelial cell hyperproliferation includes reducing or ameliorating at least one symptom of intestinal epithelial cell hyperproliferation in the subject.

In some embodiments, a subject is screened to determine if they would benefit from treatment with an agent that decreases expression or activity of CBP, such as a subject who has or is at risk of intestinal epithelial cell hyperproliferation, for example, using the methods discussed in Section V, above. In other embodiments, as subject who is known to be at risk of intestinal cell hyperproliferation, such a subject with one or more known risk factors for colorectal cancer or inflammatory bowel disease is determined to be a subject who would benefit from treatment with an agent that decreases expression or activity of CBP.

In some embodiments, the agent that decreases expression or activity of CBP is a specific binding agent, such as an antibody, antisense compound, or small molecule inhibitor that decreases the activity or expression of CBP. Methods of preparing antibodies against a specific target protein are well known in the art. A CBP protein or a fragment or conservative variant thereof can be used to produce antibodies which are immunoreactive or specifically bind to an epitope of CBP. Polyclonal antibodies, which consist essentially of pooled monoclonal antibodies with different epitopic specificities, as well as distinct monoclonal antibody preparations are included. The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992. The preparation of monoclonal antibodies likewise is conventional (see, for example, Kohler & Milstein, *Nature* 256:495, 1975; Coligan et al., sections 2.5.1-2.6.7; and Harlow et al. in: *Antibodies: a Laboratory Manual*, page 726, Cold Spring Harbor Pub., 1988).

Any type of antisense compound that specifically targets and regulates expression of CBP is also contemplated for use. An antisense compound is one which specifically hybridizes with and modulates expression of a target nucleic acid molecule (such as CBP). In some examples, the agent is an antisense compound selected from an antisense oligonucleotide, a siRNA, a miRNA, a shRNA or a ribozyme. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound.

In some examples, an antisense oligonucleotide is a single stranded antisense compound, such that when the antisense oligonucleotide hybridizes to a target mRNA, the duplex is recognized by RNaseH, resulting in cleavage of the mRNA. In other examples, a miRNA is a single-stranded RNA molecule of about 21-23 nucleotides that is at least partially complementary to an mRNA molecule that regulates gene expression through an RNAi pathway. In further examples, a shRNA is an RNA oligonucleotide that forms a tight hairpin, which is cleaved into siRNA. siRNA molecules are generally about 20-25 nucleotides in length and may have a two nucleotide overhang on the 3' ends, or may be blunt ended. Generally, one strand of a siRNA is at least partially complementary to a target nucleic acid. Methods of designing, preparing and using antisense compounds are within the abilities of one of skill in the art. Furthermore, sequences for CBPs (including those disclosed herein) can be identified by one of ordinary skill in the art.

Antisense compounds specifically targeting a CBP can be prepared by designing oligonucleotides that are complementary to the target nucleotide sequence, such as a mRNA sequence. Antisense compounds need not be 100% complementary to the target nucleic acid molecule to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected target nucleic acid sequence (such as nucleic acid sequences SEQ ID NOs: 3-5 disclosed herein or nucleic acid sequences associated with the GenBank accession numbers provided herein). Methods of screening antisense compounds for specificity are well known in the art (see, for example, U.S. Pat. App. Publ. No. 2003/0228689).

In additional examples, a small molecule inhibitor of CBP includes a small molecule that binds to and blocks at least one activity of a CBP, such as chitin binding, mucin binding, or GlcNAc binding, or stimulation of epithelial cell proliferation.

Inhibitors of CBP (such as a compound that decreases or blocks CBP expression or activity) can be identified by one of skill in the art, for example, utilizing the methods in Section VII, below. Methods of measuring CBP activity (such as chitin binding, mucin binding, GlcNAc binding, or stimulation of epithelial cell proliferation) are known to one of ordinary skill in the art and exemplary methods are provided in Section VII, below. Methods of measuring CBP expression are known to one of ordinary skill in the art and exemplary methods are provided in Section V, above.

Therapeutic agents can be administered to a subject in need of treatment using any suitable means known in the art. Methods of administration include, but are not limited to, intradermal, intramuscular, intraperitoneal, parenteral, subcutaneous, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent. Exemplary modes of administration are described in Section IV, above.

Administration can be accomplished by single or multiple doses. The dose required will vary from subject to subject depending on the species, age, weight and general condition of the subject, the particular therapeutic agent being used and its mode of administration. In some examples, the dose of antisense compound (such as siRNA, shRNA, or miRNA) is about 1 mg to about 1000 mg, about 10 mg to about 500 mg, or about 50 mg to about 100 mg. In some examples, the dose of antisense compound is about 1 mg, about 10 mg, about 50 mg, about 100 mg, about 250 mg, about 500 mg or about 1000 mg. In some embodiments, the dose of antisense compound is about 1.0 mg/kg to about 100 mg/kg, or about 5.0 mg/kg to about 500 mg/kg, about 10 mg/kg to about 100 mg/kg, or about 25 to about 50 mg/kg. In some examples, the dose of antisense compound is about 1.0 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg. In some embodiments, the dose of antibody is about 1 mg/kg to about 25 mg/kg, such as about 2 mg/kg to about 15 mg/kg, about 2 mg/kg to about 10 mg/kg, or about 2 mg/kg to about 8 mg/kg. In some examples, the dose of antibody is about 1 mg/kg, about 2 mg/kg, about 4 mg/kg, about 5 mg/kg, about 6 mg/kg, about 8 mg/kg, about 10 mg/kg, about 15 mg/kg, about 20 mg/kg, or about 25 mg/kg. In other embodiments, the dose of antibody is about 50 $mg/m^2$ to about 500 $mg/m^2$, such as about 50 $mg/m^2$ to about 400 $mg/m^2$, about 100 $mg/m^2$ to about 400 $mg/m^2$, or about 250 $mg/m^2$ to about 400 $mg/m^2$. In some examples, the dose is about 50 $mg/m^2$, about 100 $mg/m^2$, about 150 $mg/m^2$, about 200 $mg/m^2$, about 250 $mg/m^2$, about 300 $mg/m^2$, about 400 $mg/m^2$, or about 500 $mg/m^2$. It will be appreciated that these dosages are examples only, and an appropriate dose can be determined by one of ordinary skill in the art using only routine experimentation. The disclosed specific binding agents may also be used in combination with other treatments (such as surgery, radiation therapy, and/or chemotherapy), for example, as selected by a skilled clinician, based on the condition being treated, the age and condition of the subject and additional clinical factors.

VII. Methods of Identifying Inhibitors of Epithelial Cell Proliferation

Disclosed herein are methods for identifying inhibitors of epithelial cell proliferation (such as epithelial cell hyperproliferation). In some embodiments, the methods include contacting epithelial cells (such as intestinal epithelial cells) with a CBP and one or more test compounds and measuring the amount (such as number or percentage) of proliferating epithelial cells. A compound that decreases epithelial cell proliferation (for example, as compared to a control) is identified as an inhibitor of epithelial cell proliferation and may be selected for further testing. In some examples, the control is epithelial cells contacted with the CBP alone. In some examples, a compound that decreases epithelial cell proliferation by at least about 10%, about 20%, about 30%, about 40%, about 50%, about 60%, about 70%, about 80%, about 90%, about 95%, or even about 99%, as compared to a control is a compound that decreases epithelial cell proliferation. Such compounds may be used to inhibit epithelial cell proliferation in a subject, such as a subject with intestinal epithelial cell hyperproliferation (for example colorectal cancer, inflammatory bowel disease, celiac disease, or diabetes).

In additional embodiments, the methods for identifying an inhibitor of epithelial cell proliferation include identifying a compound that inhibits (for example, decreases) activity of a CBP. In some examples, the methods include contacting a substrate (such as chitin, mucin, or GlcNAc) with CBP and one or more test compounds and measuring the amount of activity of the CBP. A compound that decreases CBP binding to the substrate (for example, as compared to a control) is identified as an inhibitor of CBP activity and may be selected for further testing. In some examples, the control is the substrate contacted with the CBP alone. In some examples, a compound that decreases CBP activity by at least about 10%, about 20%, about 30%, about 40%, about 50%, about 60%, about 70%, about 80%, about 90%, about 95%, or even about 99%, as compared to a control is a compound that decreases CBP activity.

A "compound" or "test compound" is any substance or any combination of substances that is useful for achieving an end or result. The compounds identified using the methods disclosed herein can be of use for inhibiting epithelial cell proliferation. Any compound that has potential (whether or not ultimately realized) to inhibit epithelial cell proliferation can be tested using the methods of this disclosure.

Exemplary compounds include, but are not limited to, peptides, such as soluble peptides, including but not limited to members of random peptide libraries (see, e.g., Lam et al., Nature, 354:82-84, 1991; Houghten et al., Nature, 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., Cell, 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Methods of measuring epithelial cell proliferation are known to one of ordinary skill in the art. Such methods include in vitro or in vivo methods. In some examples, cell proliferation is measured by incorporation of a DNA label (for example 5-bromo-2-deoxyuridine (BrdU), 5-ethynyl-2'-deoxyuridine, (EdU) or [$^3$H]thymidine). In the presence of label, cells which are in S-phase incorporate the label. After an incubation period, cells which were in S-phase during the labeling period can be detected, such as by autoradiography (for cells labeled with [$^3$H]thymidine) or with fluorescently-labeled antibodies specific to BrdU (for cells labeled with BrdU), or appropriate detection reagents (for EdU, such as CLICK-IT EdU kit, Invitrogen). A decrease in the number of labeled cells (such as a decrease of at least about 10%, about 20%, about 30%, about 40%, about 50%, about 60%, about 70%, about 80%, about 90%, about 95%, or even about 99%) in the presence of CBP and one or more test compounds as compared to in the presence of CBP without the test compound indicates that the compound inhibits cell proliferation.

In other examples, cell proliferation is measured by detecting cellular DNA content in a population of cells, as DNA content is closely proportional to cell number. Such methods include detecting a dye that binds to nucleic acids (such as CYQUANT cell proliferation kit, Invitrogen). In other examples, cell proliferation is measured by quantifying cleavage of a tetrazolium salt (such as MTT, XTT, or MTS) to insoluble formazan crystals by mitochondrial dehydrogenase. One of ordinary skill in the art can identify additional methods to measure epithelial cell proliferation.

Methods of measuring CBP activity, such as binding to chitin and/or mucin are known to one of ordinary skill in the art. In some examples, the methods include incubating CBP with a substrate (such as α-chitin, β-chitin, colloidal chitin, chitin beads, GlcNAc beads, or mucin). Binding (such as amount of binding) of the CBP to the substrate can be determined by gel electrophoresis, ELISA, or other methods known to one of skill in the art.

In addition to or as an alternative to the above, the following embodiments are described:

Embodiment 1 is directed to a method for increasing intestinal epithelial cell proliferation, comprising contacting intestinal epithelial cells with an isolated chitin binding protein, or a portion thereof.

Embodiment 2 is directed to embodiment 1, wherein the chitin binding protein comprises a protein with at least 90% sequence identity to SEQ ID NO: 1 or SEQ ID NO: 2, or a portion thereof.

Embodiment 3 is directed to embodiment 2, wherein the chitin binding protein comprises the amino acid sequence of SEQ ID NO: 1 or SEQ ID NO: 2, or a portion thereof.

Embodiment 4 is directed to embodiment 1, wherein the chitin binding protein comprises a protein with at least 90% sequence identity amino acids 25-193 of SEQ ID NO: 1 or amino acids 25-404 of SEQ ID NO: 1.

Embodiment 5 is directed to embodiment 4, wherein the chitin binding protein comprises the amino acid sequence of amino acids 25-193 of SEQ ID NO: 1 or amino acids 25-404 of SEQ ID NO: 1.

Embodiment 6 is directed to any one of embodiments 1 to 5, wherein contacting the intestinal epithelial cells with the isolated chitin binding protein comprises administering the isolated chitin binding protein to a subject.

Embodiment 7 is directed to any one of embodiments 1 to 8, wherein the subject is a subject in need of increased intestinal epithelial cell proliferation.

Embodiment 8 is directed to embodiment 7, wherein the subject in need of increased intestinal epithelial cell proliferation is a subject with short bowel syndrome, Hirschsprung's disease, or necrotizing enterocolitis.

Embodiment 9 is directed to a method of identifying a subject having or being at risk of hyperproliferation of intestinal epithelial cells, comprising: determining presence or amount of a chitin binding protein in a sample from the subject; comparing the presence or amount of the chitin binding protein in the sample from the subject with a control; and identifying the subject as having or being at risk of hyperproliferation of intestinal epithelial cells if the presence or amount of the chitin binding protein in the sample from the subject is greater than the control.

Embodiment 10 is directed to embodiment 9, wherein the chitin binding protein comprises a protein with at least 90% sequence identity to SEQ ID NO: 1 or SEQ ID NO: 2, or a portion thereof.

Embodiment 11 is directed to embodiment 8, wherein the chitin binding protein comprises the amino acid sequence of SEQ ID NO: 1 or SEQ ID NO: 2, or a portion thereof.

Embodiment 12 is directed to embodiment 9, wherein the chitin binding protein comprises a protein with at least 90% sequence identity amino acids 25-193 of SEQ ID NO: 1 or amino acids 25-404 of SEQ ID NO: 1.

Embodiment 13 is directed to embodiment 12, wherein the chitin binding protein comprises the amino acid sequence of amino acids 25-193 of SEQ ID NO: 1 or amino acids 25-404 of SEQ ID NO: 1.

Embodiment 14 is directed to any one of embodiments 9 to 13, wherein the subject is a subject having or suspected of having colorectal cancer, inflammatory bowel disease, irritable bowel syndrome, celiac disease, or diabetes.

Embodiment 15 is directed to any one of embodiments 9 to 14, wherein the sample comprises blood, fine needle aspirate, urine, saliva, tissue biopsy, surgical specimen, or autopsy material.

Embodiment 16 is directed to any one of embodiments 9 to 15, further comprising administering to the subject an inhibitor of the chitin binding protein.

Embodiment 17 is directed to embodiment 16, wherein the inhibitor of the chitin binding protein comprises an antibody, an antisense nucleic acid, or a small molecule inhibitor of the chitin binding protein.

Embodiment 18 is directed to a method of decreasing intestinal epithelial cell proliferation in a subject, comprising administering to the subject an inhibitor of a chitin binding protein.

Embodiment 19 is directed to embodiment 18, wherein the inhibitor of the chitin binding protein comprises an antibody, an antisense nucleic acid, or a small molecule inhibitor of the chitin binding protein.

Embodiment 20 is directed to embodiment 18 or 19, wherein the inhibitor of the chitin binding protein decreases the expression or activity of the chitin binding protein.

Embodiment 21 is directed to a method for treating intestinal cell hyperproliferation in a subject comprising administering a compound that blocks chitin binding protein activity.

Embodiment 22 is directed to embodiment 21, wherein the compound that blocks chitin binding activity comprises an antibody, an antisense nucleic acid, or a small molecule inhibitor of the chitin binding protein.

Embodiment 23 is directed to any one of embodiments 20 to 22, wherein activity of the chitin binding protein comprises chitin binding, mucin binding, N-acetyl glucosamine binding or stimulation of epithelial cell proliferation.

Embodiment 24 is directed to any one of embodiments 18 to 23, wherein the subject comprises a subject having or at risk of increased intestinal epithelial cell hyperproliferation.

Embodiment 25 is directed to embodiment 24, wherein the subject is a subject having or suspected of having colorectal cancer, inflammatory bowel disease, irritable bowel syndrome, celiac disease, or diabetes.

The following examples are provided to illustrate certain particular features and/or embodiments. These examples should not be construed to limit the disclosure to the particular features or embodiments described.

Example 1

Secreted *A. veronii* Factor Promoting Intestinal Epithelial Cell Proliferation This example describes identification of a secreted factor from *A. veronii* that promotes intestinal epithelial cell proliferation.

Previous work showed that zebrafish larvae reared germ-free (GF) had reduced proliferation of intestinal epithelial cells as compared to conventionally reared (CV) zebrafish larvae (Cheesman et al., *Proc. Natl. Acad. Sci. USA* 108: 4570-4577, 2011; incorporated herein by reference). In addition, zebrafish larvae reared in monoassociation with *Aeromonas veronii* or GF with a cell-free supernatant (CFS) from *Aeromonas veronii* had similar levels of intestinal epithelial cell proliferation as conventionally reared zebrafish (Cheesman et al.).

Zebrafish larvae intestinal epithelial cell proliferation was determined by counting 5-ethynyl-2'-deoxyridine (EdU)-labeled cells. Larvae were immersed in 100 µg/mL EdU (catalog number A10044; Invitrogen) for 16 hours before termination of the experiment. Larvae were fixed in 4% paraformaldehyde, and then paraffin embedded, and cut into 7-µm sections. For EdU detection, slides were processed according to the Click-iT® EdU Cell Proliferation Assay Kit (catalog number C35002; Molecular Probes). EdU-labeled nuclei within the intestinal epithelium were counted over 30 serial 7 µm sections beginning at the esophageal-intestinal junction and proceeding caudally into the bulb. Analysis of this extended region was necessary because of the stochastic patterns of cell proliferation observed.

In order to identify the factor secreted by *A. veronii*, CFS was prepared from wild-type *A. veronii* and a mutant (Δt2ss) lacking the type II secretion system. Zebrafish larvae reared GF in the presence of CFS from wild-type *A. veronii* had levels of proliferating intestinal epithelial cells similar to CV-reared zebrafish, while zebrafish larvae reared GF in the presence of CFS from Δt2ss *Aeromonas veronii* had similar levels of proliferating intestinal epithelial cells as GF-reared zebrafish (FIG. 1).

Mass spectrometry was used to compare CFS from wild-type and Δt2ss *A. veronii*. The 300 most abundant proteins present were identified and the two samples were compared to identify proteins present in wild-type CFS but not Δt2ss CFS (Table 1).

TABLE 1

Comparison of proteins in wild-type and Δt2ss *Aeromonas veronii* CFS

| Protein | WT | T2SS mutant |
| --- | --- | --- |
| Chitin-binding protein, carbohydrate-binding | 120 | 8 |
| Metalloprotease | 119 | 6 |
| Protease | 105 | 0 |
| Putative trimethylamine-N-oxide reductase | 72 | 0 |
| Chitinase, putative | 72 | 0 |
| Putative uncharacterized protein | 61 | 1 |
| Collagenase family | 55 | 2 |
| Aeromonas virulence factor | 46 | 1 |
| Serine protease Ahe2 | 44 | 0 |
| Chitinase A | 29 | 0 |
| Pullulanase | 25 | 1 |
| UshA protein | 20 | 0 |
| Chitinase | 18 | 0 |
| Glycoside hydrolase family 18 | 14 | 1 |
| Chitinase 92 | 12 | 0 |
| Twin-arginine translocation pathway signal | 12 | 0 |
| Predicted extracellular nuclease | 11 | 0 |
| 2',3'-cyclic-nucleotide 2'-phosphodiesterase | 9 | 0 |

Figure 2:
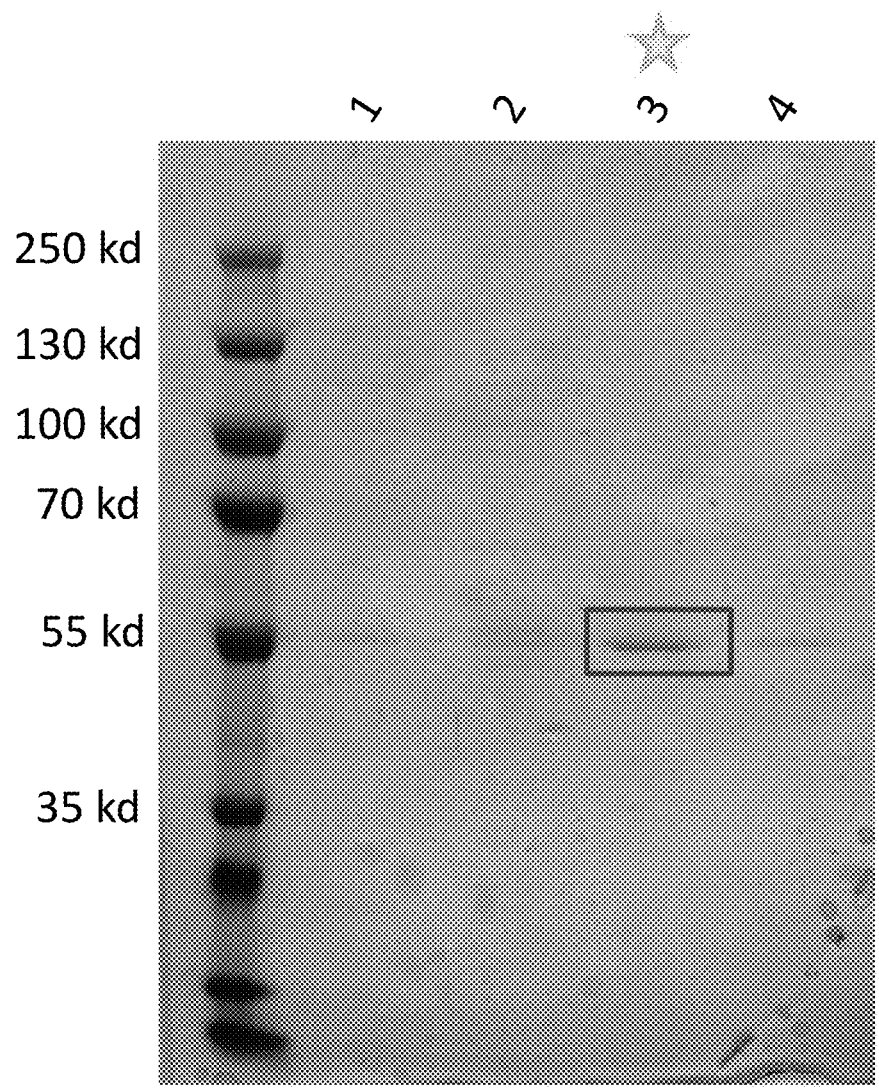
FIG. 2 is a digital image of Coomassie-blue stained SDS-PAGE of *A. veronii* CFS fractions. Fraction 3 (star) had the highest proliferative activity.

The CFS was fractionated by ammonium sulfate precipitation, and fractions were tested for their proliferative activity on intestinal epithelial cells. The proliferative activity was concentrated in one fraction. The fractions were analyzed by SDS-PAGE and the active fraction was found to contain one dominant protein of about 55 kD (FIG. 2). The molecular weight of the proteins with increased amounts in wild-type versus Δt2ss *A. veronii* was considered (Table 2). Mass spectrometry showed that chitin-binding protein (CBP) was enriched in the active fraction.

TABLE 2

Molecular weight of candidate *Aeromonas veronii* proliferative proteins

| Protein | MW (kD) |
| --- | --- |
| Chitin-binding protein, carbohydrate-binding | 51.9 |
| Metalloprotease | 109.3 |
| Protease | 63.7 |
| Putative trimethylamine-N-oxide reductase | 91.9 |
| Chitinase, putative | 69.6 |
| Putative uncharacterized protein | 130.5 |
| Collagenase family | 103.6 |
| Aeromonas virulence factor | 53.9 |
| Serine protease Ahe2 | 66.7 |
| Chitinase A | 93.1 |
| Pullulanase | 145.5 |
| UshA protein | 61.7 |
| Chitinase | 107.8 |
| Glycoside hydrolase family 18 | 79 |
| Chitinase 92 | 92.1 |
| Twin-arginine translocation pathway signal | 70.5 |
| Predicted extracellular nuclease | 78.4 |
| 2',3'-cyclic-nucleotide 2'-phosphodiesterase | 73.3 |

Figure 3:
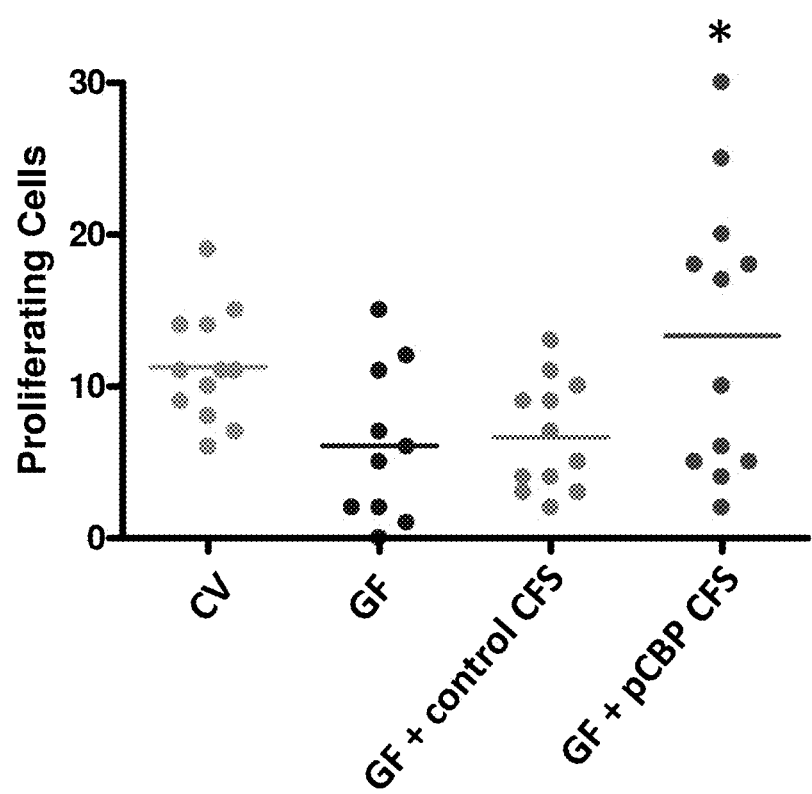
FIG. 3 is a graph showing the number of proliferating intestinal epithelial cells in zebrafish raised conventionally (CV), germ-free (GF), GF with CFS from *E. coli* not expressing CBP (GF+control CFS), or GF with CFS from *E. coli* expressing *A. veronii* CBP (GF+pCBP CFS). *, significantly more than GF.

To test the activity of *Aeromonas veronii* CBP (SEQ ID NO: 1), it was cloned and expressed in *E. coli*. The *E. coli* genome does not contain a CBP homologue, and CFS from control *E. coli* expressing the empty cloning vector without the CBP sequence did not have any proliferation-inducing activity. CFS from the recombinant *E. coli* was applied to GF-reared zebrafish and increased intestinal cell proliferation compared to GF-reared zebrafish, to levels similar to CV-reared zebrafish (FIG. 3).

Figure 4:
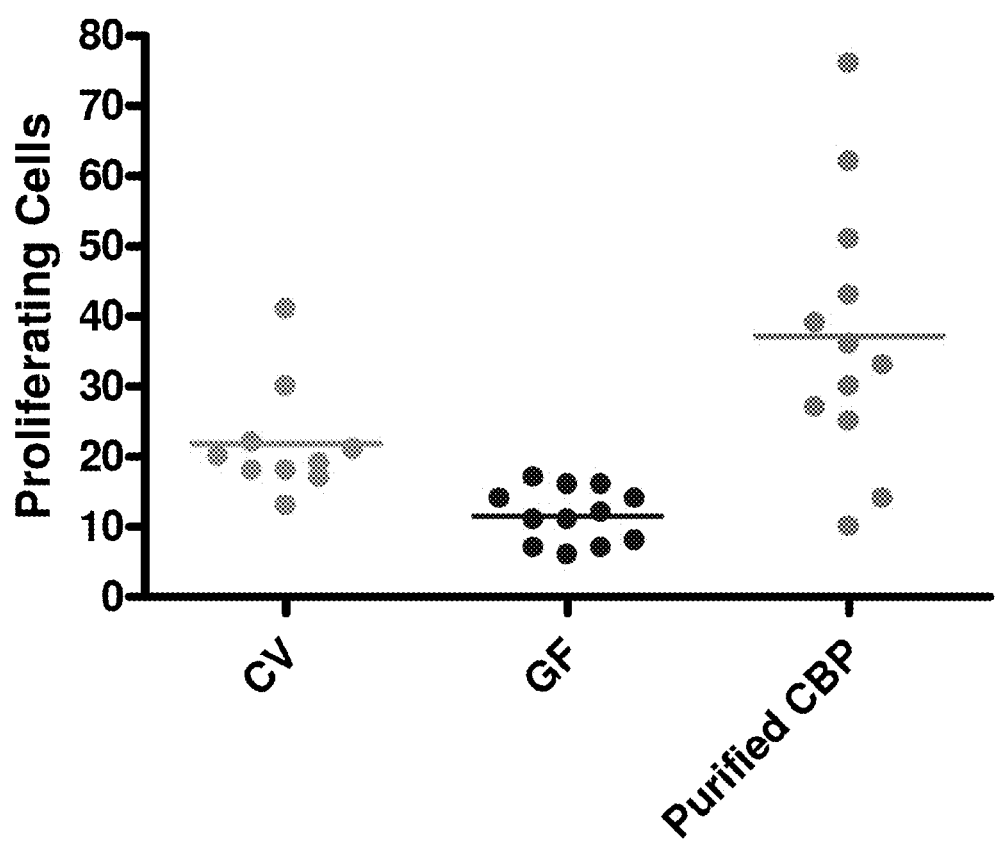
FIG. 4 is a graph showing the number of proliferating intestinal epithelial cells in zebrafish raised conventionally (CV), germ-free (GF), or GF with purified *A. veronii* CBP. *, significantly more than GF.

Finally, the ability of purified *A. veronii* CBP to promote intestinal epithelial cell proliferation was tested. CBP was tagged with GST on the N-terminus. The protein was purified via GST resin and the GST tag removed with precision protease. Fish were exposed to 50 ng/mL CBP. As shown in FIG. 4, Purified *A. veronii* CBP promoted intestinal epithelial cell proliferation, indicating that CBP alone was sufficient to promote cell proliferation.

Example 2

Effect of *Vibrio cholerae* GbpA Protein on Intestinal Epithelial Cell Proliferation This example describes identification of a *V. cholerae* protein that promotes intestinal epithelial cell proliferation.

Figure 5:
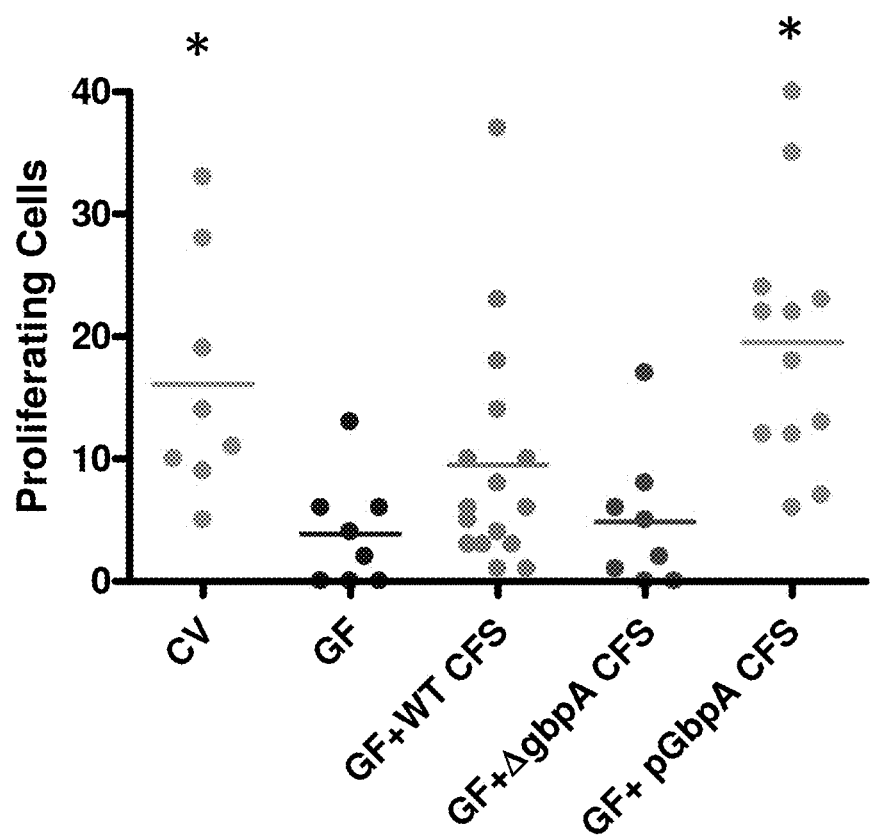
FIG. 5 is a graph showing the number of proliferating intestinal epithelial cells in zebrafish raised conventionally (CV), germ-free (GF), GF with CFS from *Vibrio cholerae* (GF+WT CFS), GF with CFS from N-acetylglucosamine binding protein A (GbpA) deletion mutant *V. cholerae* (GF+ΔgbpA CFS), or GF with CFS from pGbpA complementation *V. cholerae* (GF+pGbpA CFS). *, significantly more than GF.

The *A. veronii* CBP identified in Example 1 is homologous to *Vibrio cholerae* N-acetylglucosamine binding protein A (GbpA), which binds to GlcNAc residues in chitin and mucin. CFS was prepared from wild-type and ΔgbpA *V. cholerae* strains and applied to GF-reared zebrafish. The CFS from wild-type *V. cholerae* slightly (but not significantly) increased intestinal epithelial cell proliferation in GF-reared zebrafish compared to untreated GF-reared zebrafish (FIG. 5). In addition, CFS from a *V. cholerae* GbpA complementation strain was applied to GF-reared zebrafish and increased intestinal cell proliferation compared to GF-reared zebrafish, to levels similar to CV-reared zebrafish (FIG. 5).

Figure 6:
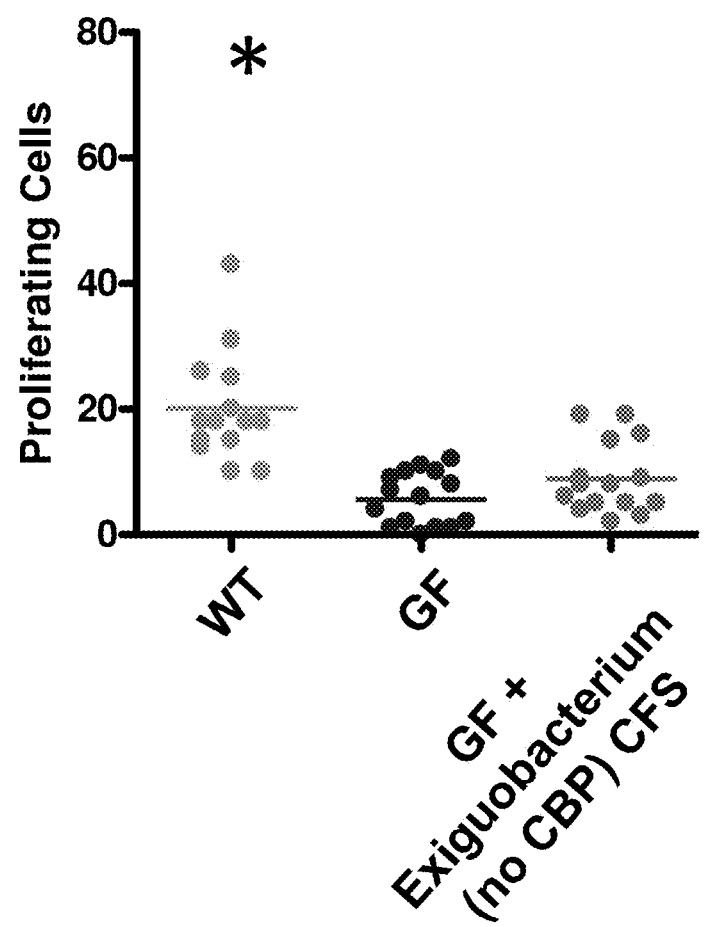
FIG. 6 is a graph showing the number of proliferating intestinal epithelial cells in zebrafish raised conventionally (CV), germ-free (GF), or GF with CFS from *Exiguobacterium* (GF+*Exiguobacterium* CFS). *, significantly more than GF.

To determine whether additional members of the microbiota secrete a factor that promotes cell proliferation, CFS from *Exiguobacterium* (which does not have a sequence homologous to CBP) was applied to GF-reared zebrafish. The CFS from *Exiguobacterium* did not significantly increase cell proliferation over that of untreated GF-reared zebrafish (FIG. 6).

Example 3

Determination of CBP Regions with Cell Proliferation Promoting Activity

This example describes identification of a domain of CBP that promotes intestinal epithelial cell proliferation.

Figure 7:
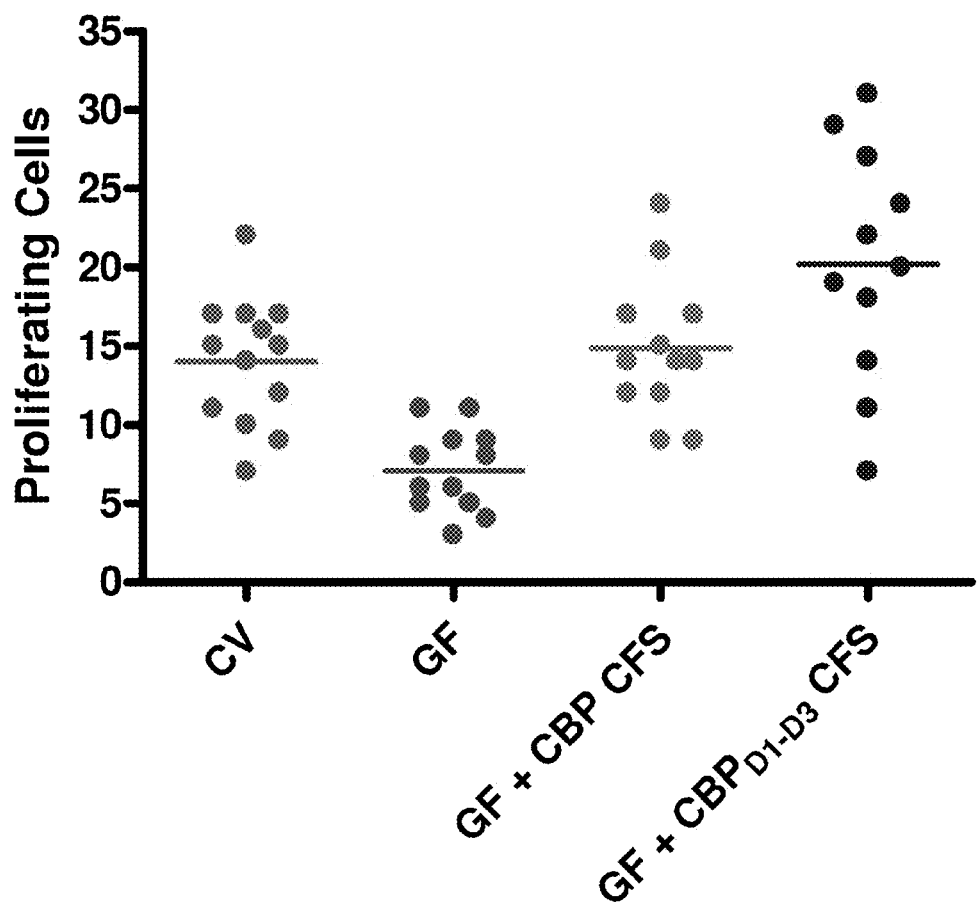
FIG. 7 is a graph showing the number of proliferating intestinal epithelial cells in zebrafish raised conventionally (CV), germ-free (GF), GF with CFS from *E. coli* expressing full-length CBP (GF+CBP CFS), or GF with CFS from *E. coli* expressing *A. veronii* CBP with domain D4 removed (CF+ $CBP_{D1-D3}$ CFS). *, significantly more than GF.
Figure 8:
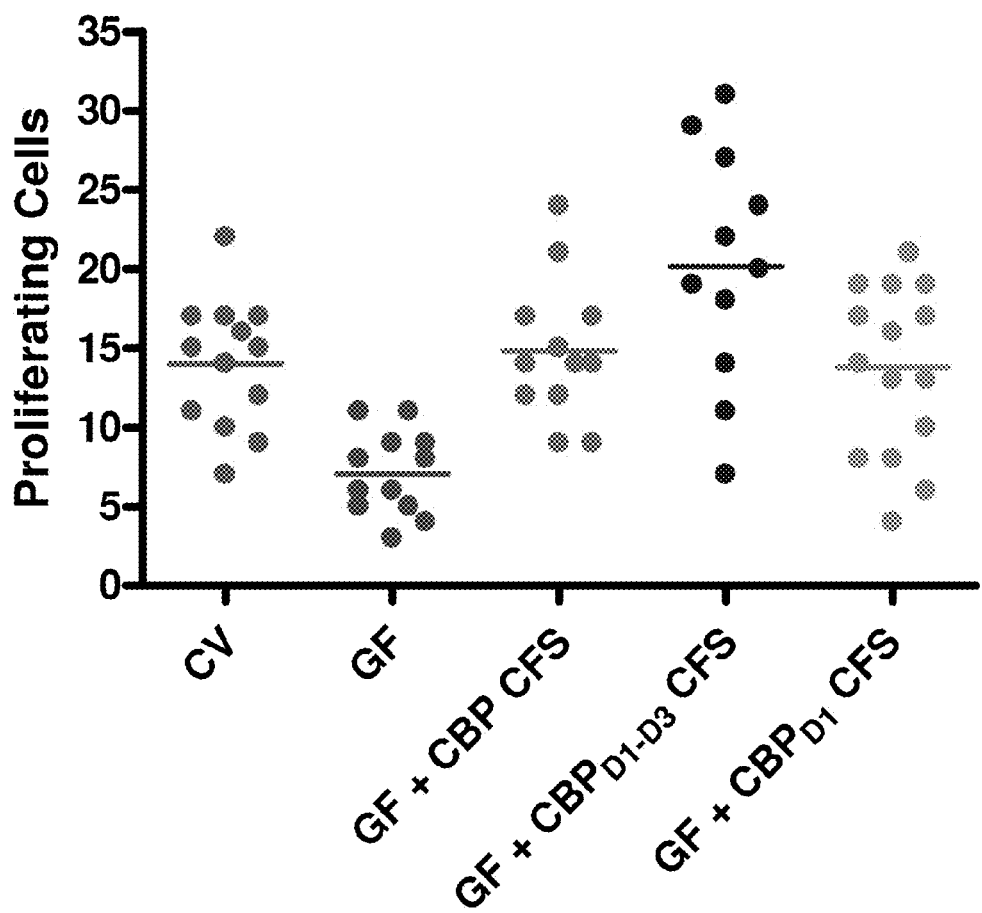
FIG. 8 is a graph showing the number of proliferating intestinal epithelial cells in zebrafish raised conventionally (CV), germ-free (GF), GF with CFS from *E. coli* expressing full-length CBP (GF+CBP CFS), GF with CFS from *E. coli* expressing *A. veronii* CBP with domain D4 removed (GF+ $CBP_{D1-D3}$ CFS), or GF with CFS from *E. coli* expressing *A. veronii* CBP domain D1 alone (GF+$CBP_{D1}$ CFS). *, significantly more than GF.

The *V. cholerae* GbpA protein has four domains (D1-D4) (Wong et al., *PLoS Pathogens* 8:e1002373, 2012). Domains D1 and D4 have structural and sequence similarity to chitin binding proteins and were previously shown to bind to chitin (Wong et al.). Mutagenesis studies were performed to determine whether these chitin binding domains were required for intestinal epithelial cell proliferation. A truncation mutant that removed domain 4 of *A. veronii* CBP ($CBP_{D1-D3}$) was constructed and expressed in *E. coli*. CFS from the recombinant *E. coli* was applied to GF-reared zebrafish and increased intestinal cell proliferation compared to GF-reared zebrafish, to levels similar to (or even higher than) CV-reared zebrafish or CFS with full-length CBP (FIG. 7). A truncated *A. veronii* CBP consisting of D1 alone was also constructed and expressed in *E. coli*. CFS from the recombinant *E. coli* was applied to GF-reared zebrafish and increased intestinal cell proliferation compared to GF-reared zebrafish, to levels similar to (or even higher than) CV-reared zebrafish or CFS with full-length CBP (FIG. 8).

Figure 9:
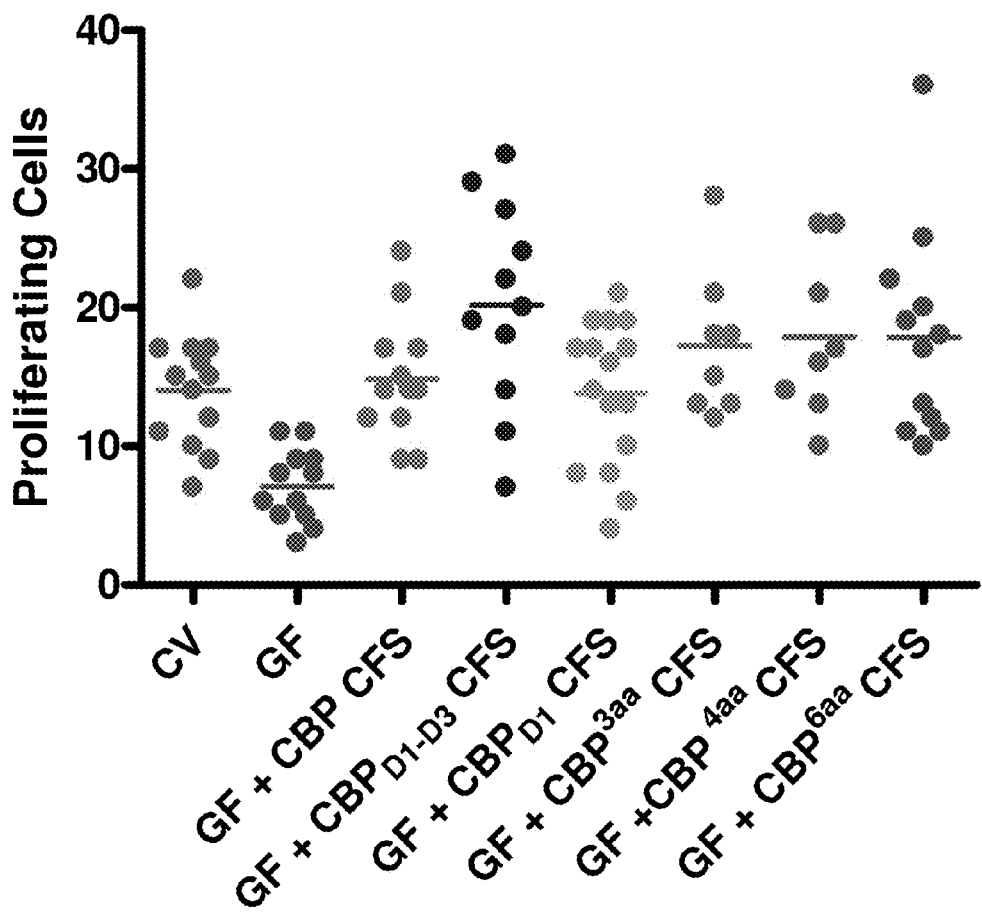
FIG. 9 is a graph showing the number of proliferating intestinal epithelial cells in zebrafish raised conventionally (CV), germ-free (GF), GF with CFS from *E. coli* expressing full-length CBP (GF+CBP CFS), GF with CFS from *E. coli* expressing *A. veronii* CBP with domain D4 removed (GF+ $CBP_{D1-D3}$ CFS), GF with CFS from *E. coli* expressing *A. veronii* CBP domain D1 alone (GF+$CBP_{D1}$ CFS), or GF with CFS from *E. coli* expressing *A. veronii* CBP with three, four, or six amino acid mutations. $CBP^{3aa}$ indicates *A. veronii* CBP with W51A, E52A, and E57A mutations $CBP^{4aa}$ indicates *A. veronii* CBP with W51A, E52A, E57A, and H111A mutations; and $CBP^{6aa}$ indicates *A. veronii* CBP with W51A, E52A, E57A, H111A, D178A, and N181A mutations. *, significantly more than GF.

The *A. veronii* CBP domain 1 is a member of the CBP21 family of chitin binding proteins, which appear to bind to chitin through six highly conserved residues (Vaaje-Kolstad et al., *J. Biol. Chem.* 280:11313-11319, 2005). These residues are conserved in the *A. veronii* CBP D1 (W51, E52, E57, H111, D178, and N181 of SEQ ID NO: 1). The *A. veronii* CBP also includes a conserved residue predicted to be important for chitinase enzymatic activity (H25 of SEQ ID NO: 1); however, chitinase activity has never been directly shown for CBPs. *A. veronii* CBPs with alanine substitutions at one or more of the six chitin binding positions were made and expressed in *E. coli*. CBP proteins with three, four, or six alanine substitutions were at least as effective at promoting intestinal epithelial cell proliferation as the wild type full-length CBP (FIG. 9). Thus, the conserved chitin binding residues do not appear to be required for cell proliferation-promoting activity of CBP.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of increasing epithelial cell proliferation, comprising contacting epithelial cells with an isolated chitin binding protein comprising at least 95% sequence identity to one of SEQ ID NOs: 1 or 2, thereby increasing epithelial cell proliferation.

2. The method of claim 1, wherein the chitin binding protein comprises the amino acid sequence of SEQ ID NOs: 1 or 2.

3. The method of claim 1, wherein the chitin binding protein consists of SEQ ID NO: 1 or 2.

4. The method of claim 1, wherein the epithelial cells comprise intestinal epithelial cells.

5. The method of claim 1, wherein contacting epithelial cells with the isolated chitin binding protein comprises administering the isolated chitin binding protein to a subject.

6. The method of claim 5, wherein the subject is a subject in need of increased epithelial cell proliferation.

7. The method of claim 6, wherein the subject in need of increased epithelial cell proliferation is a subject with short bowel syndrome, Hirschsprung's disease, or necrotizing enterocolitis.

8. A method of increasing epithelial cell proliferation, comprising contacting epithelial cells with an isolated protein comprising an amino acid sequence with at least 95% sequence identity to amino acids 25-193 of SEQ ID NO: 1 or comprising an amino acid sequence with at least 95% sequence identity to amino acids 25-404 of SEQ ID NO: 1, thereby increasing epithelial cell proliferation.

9. The method of claim 8, wherein the isolated protein comprises amino acids 25-193 of SEQ ID NO: 1 or amino acids 25-404 of SEQ ID NO: 1.

10. The method of claim 9, wherein the isolated protein consists of amino acids 25-193 of SEQ ID NO: 1 or amino acids 25-404 of SEQ ID NO: 1.

11. The method of claim 8, wherein the epithelial cells comprise intestinal epithelial cells.

12. The method of claim 8, wherein contacting epithelial cells with the isolated protein comprises administering the isolated protein to a subject.

13. The method of claim 12, wherein the subject is a subject in need of increased epithelial cell proliferation.

14. The method of claim 13, wherein the subject in need of increased epithelial cell proliferation is a subject with short bowel syndrome, Hirschsprung's disease, or necrotizing enterocolitis.

* * * * *